United States Patent [19]

Umezawa et al.

[11] Patent Number: 4,873,225

[45] Date of Patent: Oct. 10, 1989

[54] 1-N-(4-AMINO-3-FLUORO-2-HYDROX-YBUTYRYL)-KANAMYCINS

[75] Inventors: Sumio Umezawa, Tokyo; Tsutomu Tsuchiya, Yokohama; Tomio Takeuchi, Tokyo; Kazuo Umezawa, Tokyo; Yoshiaki Takahashi, Tokyo; Tetsuo Shitara, Tokyo; Yoshihiko Kobayashi; Yasushi Takagi, both of Yokohama, all of Japan

[73] Assignee: Zaidan Hojin Biseibutsu Kagaku Kenkyu Kai, Japan

[21] Appl. No.: 158,628

[22] Filed: Feb. 22, 1988

[30] Foreign Application Priority Data

Feb. 24, 1987 [JP] Japan .................................. 62-39033

[51] Int. Cl.$^4$ ...................... A61K 31/70; C07H 15/22
[52] U.S. Cl. ..................................... 514/41; 536/13.7; 536/13.8
[58] Field of Search ................. 536/13.7, 13.8; 514/41

[56] References Cited

U.S. PATENT DOCUMENTS

4,170,642 10/1979 Umezawa et al. ..................... 514/41
4,634,688 1/1987 Umezawa et al. ..................... 514/41

*Primary Examiner*—Ronald W. Griffin
*Assistant Examiner*—Elli Peselev
*Attorney, Agent, or Firm*—Lalos & Keegan

[57] ABSTRACT

As new compound are now provided ten compounds, namely 1-N-{(2R,3R)-4-amino-3-fluoro-2-hydroxybutyryl}kanamycin A; 1-N-{(2R,3R)-4-amino-3-fluoro-2-hydroxybutyryl}-2',3'-dideoxykanamycin A; 1-N-{(2R,3R)-4-amino-3-fluoro-2-hydroxybutyryl}-2',3'-dideoxy-2'-fluorokanamycin A; 1-N-{(2R,3R)-4-amino-3-fluoro-2-hydroxybutyryl}-5-deoxy-5-fluorokanamycin A; 1-N-{(2R,3R)-4-amino-3-fluoro-2-hydroxybutyryl}-kanamycin B; 1-N-{(2R,3R)-4-amino-3-fluoro-2-hydroxybutyryl}-3'-deoxykanamycin B; 1-N-{(2R,3R)-4-amino-3-fluoro-2-hydroxybutyryl}-3',4'-dideoxykanamycin B; 1-N-{(2R,3R)-4-amino-3-fluoro-2-hydroxybutyryl}-5-deoxy-5-fluorokanamycin B; 1-N-{(2R,3R)-4-amino-3-fluoro-2-hydroxybutyryl}-5,3'-dideoxy-5-fluorokanamycin B; and 1-N{(2R,3R)-4-amino-3-fluoro-2-hydroxybutyryl}-5,3',4'-trideoxy-5-fluorokanamycin B, which are all useful as antibacterial agent in the therapeutic treatment of bacterial infections.

13 Claims, No Drawings

1-N-(4-AMINO-3-FLUORO-2-HYDROXYBUTYRYL)-KANAMYCINS

SUMMARY OF THE INVENTION

This invention relates to various 1-N-(4-amino-3-fluoro-2-hydroxybutyryl)kanamycin A or B derivatives, which are novel semi-synthetic aminoglycosidic antibiotics, and also to a process for the production of these novel compounds. These novel compounds of this invention exhibit high antibacterial activities against a variety of kanamycin-sensitive bacteria and kanamycin-resistant bacteria and are useful as antibacterial agents.

BACKGROUND OF THE INVENTION

A wide variety of semi-synthetic aminoglycosidic antibiotics derived from kanamycin A, B or C has been known. Although these kanamycin derivatives known hithertobefore have useful antibacterial activities, their antibacterial spectra are of varying ranges, and the known kanamycin derivatives sometime may be ineffective against certain new resistant strains which may occur in future. It is hence always demaded to synthesize and provide new and still better antibacterial compounds.

We, the present inventors, succeeded in synthesizing a kanamycin A derivative having a fluorine atom substituted for the 3'-hydroxyl group, namely, 3'-deoxy-3'-fluorokanamycin A, and also we have observed that this compound is effective also against kanamycin-resistant bacteria (Japanese patent application No. 161615/84; Japanese patent application first publication "Kokai" No. 40297/86 and U.S. Pat. No. 4,634,688).

We also succeeded in synthesizing 3'-deoxy-3'-fluorokanamycin B and moreover, we confirmed that this novel compound has antibacterial activities against various gram-positive and gram-negative bacteria, including resistant strains (Japanese patent application No. 262700/84; Japanese patent application first publication "Kokai" No. 140597/86).

Also, we succeeded in making the synthesis of 3',4'-dideoxy-3'-fluorokanamycin B effective against such certain resistant strains of bacteria which produce enzymes capable of phosphorylating and/or capable of adenylating the 4'-hydroxyl group of 3'-deoxy-3'-fluorokanamycin B, for example, against Staphylococcus aureus Ap 01 and Staphylococcus epidermidis 109 (Japanese patent application No. 188525/85, Japanese patent application first publication "Kokai" No. 51694/87; U.S. patent application Ser. No. 899,100; and European patent application publication No. 0214904A2).

The present inventors also succeeded in producing 1-N-{(RS)- and (S)-3amino-2-hydroxypropionyl}- and 1-N-{(S)-4-amino-2-hydroxybutyry}-3'-deoxy-3'-fluorokanamycins A and B as novel compounds by acylating the 1-amino groups of these 3'-deoxy-3'-fluorokanamycins A and B with (RS)- or (S)-3-amino-2-hydroxypropionic acid or (S)-4-amino-2-hydroxybutyric acid, respectively. Moreover, it has been found that these novel compounds have antibacterial activities against gram-positive and gram-negative bacteria, including certain resistant strains of bacteria (see the specification of Japanese patent application No. 76706/85 and Japanese patent application first publication "Kokai" No. 236791/86).

As a result of a further investigation, the present inventors also succeeded firstly in synthesizing 2',3'-dideoxy-2'-fluorokanamycin A, and moreover we confirmed that this novel compound has antibacterial activities against gram-positive and gram-negative bacteria, including certain resistant strains of bacteria (see the specification of Japanese patent application No. 263759/84; Japanese patent application first publication "Kokai" No. 143393/86; U.S. Pat. No. 4,661,474; and European patent application publication No. 0185323A2). Also the present inventors succeeded in producing 1-N-{(RS)- and (S)-3-amino-2-hydroxypropionyl}-and 1-N-{(S)-4-amino-2-hydroxybutyl}-2', 3'-dideoxy-2'-fluorokanamycins A as novel compounds by acylating the 1-amino group of the 2',3'-dideoxy-2'-fluorokanamycin A, with (RS)- or (S)-3-amino-2-hydroxypropionic acid or (S)-4-amino-2-hydroxybutyric acid, respectively. Moreover, we have observed that these novel compounds have excellent antibacterial activities against gram-positive and gram-negative bacteria, including certain resistant strains of bacteria (European patent application Publication No. 0185323A2 and U.S. Pat. No. 4,661,474).

Further, we also succeeded in synthesizing 5-deoxy-5-fluorokanamycin B as a novel compound from kanamycin B and found that 5-deoxy-5-fluorokanamycin B has antibacterial activities as enhanced or improved advantageously over kanamycin B (Japanese patent application No. 181850/86, U.S. patent application Ser. No. 078,996; European patent application No. 87306904.1). We have also succeeded in synthesizing 5,3'-dideoxy-5-fluorokanamycin B from 3'-deoxykanamycin B (i.e., tobramycin), 5,4'-dideoxy-5-fluorokanamycin B from 4'-deoxykanamycin B, and 5,3',4'-trideoxy-5-fluorokanamycin B from 3',4'-dideoxykanamycin B (i.e., dibekacin). The present inventors also have made the acylation of the 1-amino group of 5-deoxy-5-fluorokanamycin B, 5,3'-dideoxy-5-fluorokanamycin B, 5,4'-dideoxy-5-fluorokanamycin B and 5,3',4'-trideoxy-5-fluorokanamycin B with (RS)-or (S)-3-amino-2-hydroxypropionyl or (S)-4-amino-2-hydroxybutyryl groups, respectively, so that their corresponding 1-N-(α-hydroxy-ω-aminoalkanoyl) derivatives are produced as novel compounds. We have also found that the latter new 1-N-acylated derivatives have further improved antibacterial activities (Japanese patent application No. 181850/86 and U.S. patent application Ser. No. 078,996 referred to above).

On the other hand, it is known that when an aminoglycosidic antibiotic acts on bacteria under acidic conditions, the antibacterial activity of this antibiotic can be decreased or become substantially null against the bacteria, even though said antibiotic can show a high and effective antibacterial activity against the bacteria when it acts on the bacteria under neutral or weakly alkaline conditions. The bacterially infected local parts (the bacterial lesions) of the living human body are not always to exist under neutral condition (pH 7.0) but may sometime exist under acidic conditions of pH 6 or more acidic conditions.

There is hence an outstanding demand for the development of such an antibacterial aminoglycosidic antibiotic or a semisynthetic derivative thereof, which can exhibit high and reliable antibacterial activities sufficient to kill bacteria effectively even when the antibacterial compound acts on the bacteria under acidic conditions of pH 6-7.

DETAILED DESCRIPTION OF THE INVENTION

The present inventors have carried out an extensive investigation in an attempt to produce such novel kanamycin derivatives which are capable of fulfilling such demands. As a result, we have succeeded for the first time to synthesize, as novel compounds, 1-N-{(2R,3R)-4-amino-3-fluoro-2-hydroxybutyryl} derivatives of kanamycin A, 2',3'-dideoxykanamycin A, 2',3'-dideoxy-2'-fluorokanamycin A, 5-deoxy-5-fluorokanamycin A, kanamycin B, 3'-deoxykanamycin B (i.e., tobramycin), 3',4'-dideoxykanamycin B (i.e., dibekacin), 5-deoxy-5-fluorokanamycin B, 5,3'-dideoxy-5-fluorokanamycin B and 5,3',4'-trideoxy-5-fluorokanamycin B. Moreover, we have also found that these 1-N-{(2R,3R)-4-amino-3-fluoro-2-hydroxybutyryl}-kanamycin derivatives now synthesized exhibits not only high antibacterial activities against gram-positive bacteria, gram-negative bacteria and various kanamycin-resistant strains of bacteria but also retains high antibacterial activities even when these novel compounds act on bacteria under conditions of pH 6. In addition, 1-N-{(2R,3S)-4-amino-3-fluoro-2-hydroxybutyryl}kanamycin B was also synthesized by us, but this compound did not show any enhancement in antibacterial activities when tested in vitro. The present invention has been completed on the basis of these above findings.

In a first aspect of this invention, there is thus provided a 1-N-{(2R,3R)-4-amino-3-fluoro-2-hydroxybutyryl}kanamycin A or B derivative represented by the general formula:

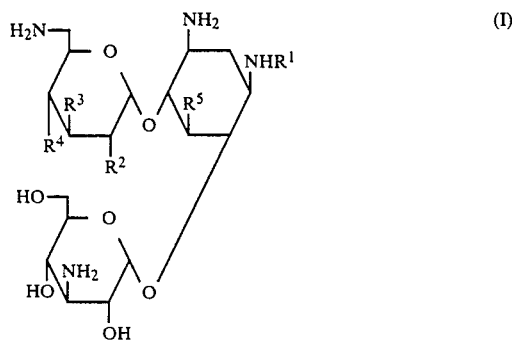

wherein $R^1$ means a (2R,3R)-4-amino-3-fluoro-2-hydroxybutyryl group of the formula:

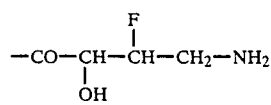

and (a) $R^2$, $R^3$, $R^4$ and $R^5$ are each a hydroxyl group, or (b) $R^4$ and $R^5$ are each a hydroxyl group, and $R^2$ and $R^3$ are each a hydrogen atom, or (c) $R^4$ and $R^5$ are each a hydroxyl group, $R^3$ is a hydrogen atom, and $R^2$ is a fluorine atom, or (d) $R^2$, $R^3$ and $R^4$ are each a hydroxyl group, and $R^5$ is a fluorine atom, or (e) $R^2$ is an amino group, and $R^3$, $R^4$ and $R^5$ are each a hydroxyl group, or (f) $R^2$ is an amino group, $R^3$ is a hydrogen atom, and $R^4$ and $R^5$ are each a hydroxyl group, or (g) $R^2$ is an amino group, $R^3$ and $R^4$ are each a hydrogen atom, and $R^5$ is a hydroxyl group, or (h) $R^2$ is an amino group, $R^3$ and $R^4$ are each a hydroxyl group, and $R^5$ is a fluorine atom, or (i) $R^2$ is an amino group, $R^3$ is a hydrogen atom, $R^4$ is a hydroxyl group, and $R^5$ is a fluorine atom, or (j) $R^2$ is an amino group, $R^3$ and $R^4$ are each a hydrogen atom, and $R^5$ is a fluorine atom; or a pharmaceutically acceptable acid addition salt thereof.

Illustrative examples of the kanamycin A or B derivative of the general formula (I) according to the first aspect of this invention may include the following ten compounds. These compounds are each in the form of a basic, colorless powdery substance and exhibits no definite melting point. Their chemical names will hereinafter be listed, followed by their respective specific optical rotations.

(1) 1-N-{(2R,3R)-4-Amino-3-fluoro-2-hydroxybutyryl}-kanamycin A {in the general formula (I), $R^1$ is a (2R,3R)-4-amino-3-fluoro-2-hydroxybutryl group, and $R^2$, $R^3$, $R^4$ and $R^5$ are individually a hydroxyl group} (Invention Compound No. 1).
$[\alpha]_D^{24}$ +82° (c 0.5, water).

(2) 1-N-{(2R,3R)-4-Amino-3-fluoro-2-hydroxybutyryl}-2',3'-dideoxykanamycin A {in the general formula (I), $R^1$ is a (2R,3R)-4-amino-3-fluoro-2-hydroxybutyryl group, $R^2$ and $R^3$ are individually a hydrogen atom, and $R^4$ and $R^5$ are individually a hydroxyl group } (Invention Compound No. 2).
$[\alpha]_D^{24}$ +85° (c 0.5, water).

(3) 1-N-{(2R,3R)-4-Amino-3-fluoro-2-hydroxybutyryl}-2',3'-dideoxy-2'-fluorokanamycin A {in the general formula (I), $R^1$ is a (2R,3R)-4-amino-3-fluoro-2-hydroxybutyryl group, $R^2$ is a fluorine atom, $R^3$ is a hydrogen atom, and $R^4$ and $R^5$ are individually a hydroxyl group} (Invention Compound No. 3).
$[\alpha]_D^{24}$ +82° (c 0.5, water).

(4) 1-N-{(2R,3R)-4-Amino-3-fluoro-2-hydroxybutyryl}-5-deoxy-5-fluorokanamycin A {in the general formula (I), $R^1$ is a (2R,3R)-4-amino-3-fluoro-2-hydroxybutyryl group, $R^2$, $R^3$ and $R^4$ are individually a hydroxyl group, and $R^5$ is a fluorine atom} (Invention Compound No. 4).
$[\alpha]_D^{24}$ +84° (c 0.5, water).

(5) 1-N-{(2R,3R)-4-Amino-3-fluoro-2-hydroxybutyryl}-kanamycin B {in the general formula (I), $R^1$ is a (2R,3R)-4-amino-3-fluoro-2-hydroxybutyryl group, $R^2$ is an amino group, and $R^2$, $R^4$ and $R^5$ are individually a hydroxyl group} (Invention Compound No. 5).
$[\alpha]_D^{20}$ +80° (c 1, water).

(6) 1-N-{(2R,3R)-4-Amino-3-fluoro-2-hydroxybutyryl}-3'-deoxykanamycin B {in the general formula (I), $R^1$ is a (2R,3R)-4-amino-3-fluoro-2-hydroxybutyryl group, $R^2$ is an amino group, $R^4$ and $R^5$ are individually a hydroxyl group, and $R^3$ is a hydrogen atom} (Invention Compound No. 6).
$[\alpha]_D^{24}$ +73° (c 0.5, water).

(7) 1-N-{(2R,3R)-4-Amino-3-fluoro-2-hydroxybutyryl}-3',4'-dideoxykanamycin B {in the general formula (I), $R^1$ is a (2R,3R)-4-amino-3-fluoro-2-hydroxybutyryl group, $R^2$ is an amino group, $R^3$ and $R^4$ are individually a hydrogen atom, and $R^5$ is a hydroxyl group} (Invention Compound No. 7).
$[\alpha]_d^{19}$ +86° (c 1, water).

(8) 1-N-{(2R,3R)-4-Amino-3-fluoro-2-hydroxybutyryl}-5-deoxy-5-fluorokanamycin B {in the general formula (I), $R^1$ is a (2R,3R)-4-amino-3-fluoro-2-hydroxybutyryl group, $R^2$ is an amino group, $R^3$ and $R^4$ are individually a hydroxyl group, and $R^5$ is a fluorine atom} (Invention Compound No. 8).
$[\alpha]_D^{25}$ +81° (c 1, water).

(9) 1-N-{(2R,3R)-4-Amino-3-fluoro-2-hydroxybutyryl}-5,3'-dideoxy-5-fluorokanamycin B {in the general formula (I), $R^1$ is a (2R,3R)-4-amino-3-fluoro-2-hydroxybutyryl group, $R^2$ is an amino group, $R^3$ is a hydrogen atom, $R^4$ is a hydroxyl group, and $R^5$ is a fluorine atom} (Invention Compound No. 9).
$[\alpha]_D^{20}$ +83° (c 1, water).

(10) 1-N-{(2R,3R)-4-Amino-3-fluoro-2-hydroxybutyryl}-5,3',4'-trideoxy-5-fluorokanamycin B {in the general formula (I), $R^1$ is a (2R,3R)-4-amino-3-fluoro-2-hydroxybutyryl group, $R^2$ is an amino group, $R^3$ and $R^4$ are individually a hydrogen atom, and $R^5$ is a fluorine atom} (Invention Compound No. 10).
$[\alpha]_D^{20}$ +86° (c 1, water).

Antibacterial activities of each of the abovementioned compounds of the general formula (I) according to this invention were determined by measuring their minimum growth inhibitory concentrations (MIC, mcg/ml) against various bacteria in accordance with a standard serial dilution method. The pH condition of the incubation medium where the MIC data were measured was set at pH 7, unless otherwise specifically indicated. Antibacterial spectra of Invention Compound Nos. 1–10 as measured are shown in Table 1. For the sake of comparison, the antibacterial spectra of 1-N-{(S)-4-amino-2-hydroxybutyryl}kanamycin A (i.e., amikacin) and 1-N-{(S)-4-amino-2-hydroxybutyryl}-3,4-dideoxykanamycin B (i.e., habekacin) were also measured in the same manner. Results are shown in Table 1.

TABLE 1

| Bacteria tested | MIC (mcg/ml) | | | | | |
|---|---|---|---|---|---|---|
| | Invention Compound No. 1 | Invention Compound No. 2 | Invention Compound No. 3 | Invention Compound No. 4 | Amikacin (Comparative) | Invention Compound No. 5 |
| Staphylococcus aureus 209P | 1.56 | 0.2 | 0.78 | 1.56 | 1.56 | 0.78 |
| Staphylococcus aureus Ap01 | 6.25 | 1.56 | 1.56 | 6.25 | 3.12 | 6.25 |
| Bacillus subtilis PCI219 | 0.78 | 0.78 | 0.39 | 3.12 | 1.56 | 1.56 |
| Corynebacterium bovis 1810 | 0.78 | 0.78 | 0.78 | 0.39 | 1.56 | 0.39 |
| Escherichia coli K-12 | 0.39 | 0.39 | 0.2 | 0.78 | 0.78 | 0.2 |
| Escherichia coli K-12 R5 | 12.5 | 6.25 | 6.25 | 6.25 | 25 | 3.12 |
| Escherichia coli K-12 ML 1629 | 1.56 | 0.78 | 0.39 | 0.39 | 1.56 | 0.78 |
| Escherichia coli K-12 LA 290 R55 | 1.56 | 0.78 | 0.78 | 0.78 | 1.56 | 0.78 |
| Escherichia coli JR 225 | 0.78 | 0.39 | 0.39 | 0.39 | 0.78 | 0.39 |
| Escherichia coli JR66/W677 | 1.56 | 1.56 | 0.78 | 1.56 | 3.12 | 0.78 |
| Escherichia coli JR66/W677 (measured at pH 6) | 6.25 | 6.25 | 1.56 | 3.12 | 25 | 3.12 |
| Mycobacterium 607 | 1.56 | 1.56 | 0.78 | 3.12 | 1.56 | 12.5 |
| Klebsiella pneumoniae 22 #3038 | 3.12 | 3.12 | 0.78 | 3.12 | 3.12 | 3.12 |
| Proteus rettgeri GN 311 | 0.39 | 0.78 | 0.78 | 1.56 | 1.56 | 0.39 |
| Serratia marcescens | 3.12 | 3.12 | 1.56 | 6.25 | 6.25 | 6.25 |
| Providencia sp. Pv 16 | 1.56 | 1.56 | 0.78 | 1.56 | 1.56 | 1.56 |
| Pseudomonas aeruginosa A3 | 0.78 | 0.78 | 0.78 | 1.56 | 1.56 | 0.78 |
| Pseudomonas aeruginosa GN 315 | 25 | 12.5 | 12.5 | 25 | 25 | 6.25 |
| Pseudomonas aeruginosa TI 13 | 3.12 | 3.12 | 3.12 | 3.12 | 3.12 | 1.56 |
| Pseudomonas aeruginosa TI 13 (measured at pH 6) | 3.12 | 3.12 | 3.12 | 3.12 | 12.5 | 3.12 |

| Bacteria tested | MIC (mcg/ml) | | | | | |
|---|---|---|---|---|---|---|
| | Invention Compound No. 6 | Invention Compound No. 7 | Invention Compound No. 8 | Invention Compound No. 9 | Invention Compound No. 10 | Habekacin (Comparative) |
| Staphylococcus aureus 209P | 0.39 | <0.2 | 0.39 | 0.39 | 0.39 | <0.2 |
| Staphylococcus aureus Ap01 | 0.78 | 0.78 | 6.25 | 0.78 | 0.78 | 0.39 |
| Bacillus subtilis PCI219 | 0.2 | <0.2 | 0.39 | <0.2 | 0.2 | <0.2 |
| Corynebacterium bovis 1810 | 0.39 | <0.2 | 0.39 | <0.2 | <0.2 | 0.39 |
| Escherichia coli K-12 | <0.2 | <0.2 | <0.2 | <0.2 | 0.2 | 0.39 |
| Escherichia coli K-12 R5 | 3.12 | 3.12 | 3.12 | 3.12 | 3.12 | 25 |
| Escherichia coli K-12 ML 1629 | 0.78 | 0.78 | 0.78 | 0.78 | 0.39 | 0.78 |
| Escherichia coli K-12 LA 290 R55 | 0.39 | 0.39 | 0.39 | 0.39 | 0.39 | 0.78 |
| Escherichia coli JR 225 | <0.2 | 0.78 | 0.2 | 0.2 | <0.2 | 0.78 |
| Escherichia coli JR66/W677 | 0.39 | 0.78 | 0.78 | 0.39 | 0.39 | 0.78 |
| Escherichia coli JR66/W677 (measured at pH 6) | 1.56 | 1.56 | 3.12 | 1.56 | 1.56 | 6.25 |
| Mycobacterium 607 | 0.78 | 0.78 | 12.5 | 1.56 | 0.78 | 0.39 |
| Klebsiella pneumoniae 22 #3038 | 1.56 | 0.78 | 3.12 | 0.78 | 0.78 | 1.56 |
| Proteus rettgeri GN 311 | 0.39 | <0.2 | 0.2 | 0.2 | <0.2 | 0.78 |
| Serratia marcescens | 3.12 | 3.12 | 1.56 | 3.12 | 1.56 | 12.5 |
| Providencia sp. Pv 16 | 0.78 | 0.78 | 0.78 | 0.78 | 0.78 | 1.56 |
| Pseudomonas aeruginosa A3 | <0.2 | 0.39 | 0.39 | 0.2 | <0.2 | <0.2 |
| Pseudomonas aeruginosa GN 315 | 3.12 | 3.12 | 6.25 | 3.12 | 3.12 | 3.12 |
| Pseudomonas aeruginosa TI 13 | 0.78 | 0.78 | 1.56 | 0.78 | 0.78 | 0.78 |
| Pseudomonas aeruginosa TI 13 (measured at pH 6) | 3.12 | 1.56 | 6.25 | 3.12 | 3.12 | 25 |

The antibacterial activities of the novel compounds of the general formula (I) according to this invention, have advantages which are described below.

(a) The antibacterial activities of the compounds of this invention are not decreased practically even under pH conditions of pH 6–7 as compared to their antibacterial activities under neutral conditions of pH 7. This is demonstrated by the antibacterial spectra of Table 1 in which the antibacterial activities (MIC) of the compounds of this invention against Escherichia coli JR66/W677 and Pseudomonas aeruginosa TI 13 were not reduced at pH 6 as compared to those at pH 7. In contrast, the table also shows that the antibacterial activities of amikacin and habekacin, both the comparative antibiotics, against the above strains of bacteria were reduced considerably at pH 6 as compared to those at pH 7, for instance.

The 3-fluoro radical of the (2R,3R)-4-amino-3-fluoro-2-hydroxybutyryl group on the 1-amino group of each compound of the general formula (I) according to this invention has high electron-attractiveness. The present inventors have presumed that owing to the high electron-attractiveness, the terminal 4-amino group has extremely little tendency to be converted into a group in the form of $-NH_3^+$ (salt) even under acidic condition of pH 6 or under higher acidic conditions and hence can retain the form of $-NH_2$ (base), thereby to maintain the antibacterial activities of the whole compound unchanged.

(b) The compounds of this invention exhibit high antibacterial activities even against the resistant strain K-12 R5 of *Escherichia coli*, which has an enzyme {AAC(6')} capable of acetylating the 6'-$NH_2$ group of kanamycin to inactivate kanamycin. Infectious diseases by *Escherichia coli* K-12 R5 tend to increase in recent days. The compounds of this invention are therefore important for the therapeutic treatment of bacterial infections.

(c) The compounds of this invention also show high antibacterial activities against *Serratia marcescens*. The bacterial infection diseases have been being caused more and more by this bacterium in recent years.

The new compound of the general formula (I) according to this invention is usually obtained in the form of a free base, a hydrate or a carbonate thereof. The new compound of the formula (I) may, if desired, be converted into a pharmaceutically acceptable, non-toxic acid addition salt thereof in a known manner by reacting the free base form of said compound with a pharmaceutically acceptable inorganic acid such as hydrochloric acid, sulfuric acid, phosphoric acid, nitric acid and the like; or with a pharmaceutically acceptable organic acid such as acetic acid, malic acid, citric acid, ascorbic acid, methanesulfonic acid and the like.

A compound of the general formula (I) according to this invention or an acid addition salt thereof may be mixed with a pharmaceutically acceptable liquid or solid carrier or vehicle to prepare a pharmaceutical composition, especially an antibacterial composition which may be administered for therapeutic treatment of various bacterial infections in animals, including humans.

As is understood from the antibacterial data of Table 1, each of the compounds of the general formula (I) according to this invention can exhibit high antibacterial activities against a wide variety of bacteria and hence has a broad antibacterial spectrum. Moreover, they have been found to show extremely low acute toxicity against mice. For example, all mice surrived when they were orally administered with Invention Compound Nos. 1 or 2 at 150 mg/kg.

According to another aspect of this invention, therefore, there is provided a pharmaceutical composition comprising a compound of the general formula (I) as described above or a pharmaceutically acceptable acid addition salt thereof, as the active ingredient, in association with a pharmaceutically acceptable solid or liquid carrier for the active ingredient.

The pharmacuetical composition according to the aforesaid second aspect of this invention may be formulated into suitable forms for oral, parenteral or intrarectal administration. Composition in the form of injectable solution may contain 0.1% to 20.0% by weight of the compound (I) as active ingredient, and also one or more of a pH-adjuster, buffer, stabilizer, excipient, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. Suppository formulations may contain excipients and, if necessary, surfactant and lubricants additionally to the active compound.

The optimum dosage of the new compound (I) administered will, of course, depend on the mode of administration and the treatment aimed. For men, the unit dosage for injections generally contains from 50 mg to 500 mg of the compound (I), which may be administered intravenously of intramuscularly in divided doses one or more times per day. The new compound of the formula (I) used in the composition of this invention may be administered orally to an adult person at a dosage of 50 mg to 500 mg once a day.

According to a further aspect of this invention, there is provided a method of treating bacterial growth in an animal or human, which comprises administering bacteriocidally effective amount of the compound of the formula (I) as defined above or a pharmaceutically acceptable acid addition salt thereof to an animal or human infected with or susceptible to bacteria.

Process for the production of the compound of the general formula (I) according to this invention is now described.

The compounds of the general formula (I) according to this invention may be produced by a process for the production of a 1-N-{(2R,3R)-4-amino-3-fluoro-2-hydroxybutyryl}kanamycin represented by the general formula:

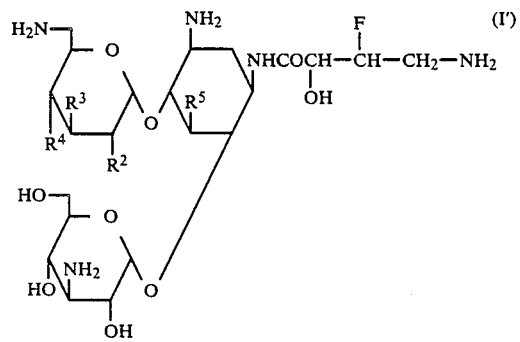

wherein $R^2$, $R^3$, $R^4$ and $R^5$ have individually the same meaning as defined in the general formula (I), given hereinbefore, which comprises (i) reacting (2R,3R)-4-azido-3-fluoro-2-hydroxybutyric acid represented by the formula:

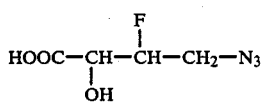

(III)

or a reactive derivative thereof with the 1-amino group of kanamycin A or B or a derivative thereof represented by the general formula:

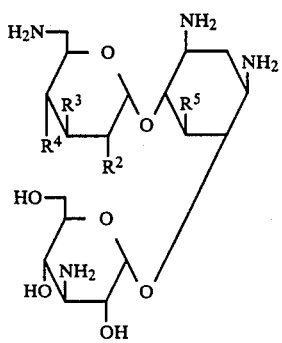

(II)

wherein $R^2$, $R^3$, $R^4$ and $R^5$ have the same meaning as defined above, or with the 1-amino group of an amino-protected derivative as obtained by protecting with an amino-protecting group some or all of the amino groups other than the 1-amino group of the compound of the formula (II), thereby to form a 1-N-acylated reaction product represented by the general formula:

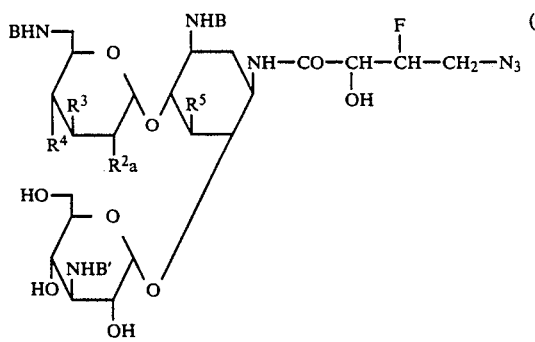

(IV)

wherein $R^2a$ means a hydroxyl group, a fluorine or hydrogen atom or a protected or unprotected amino group, $R^3$, $R^4$ and $R^5$ have the same meaning as defined above, and B and B' denote individually a hydrogen atom or stand for the amino-protecting groups which may be the same or different, (ii) reducing the azido group (—N₃) of the compound of the formula (IV) into an amino group; and then, where the resultant reduction product of general formula:

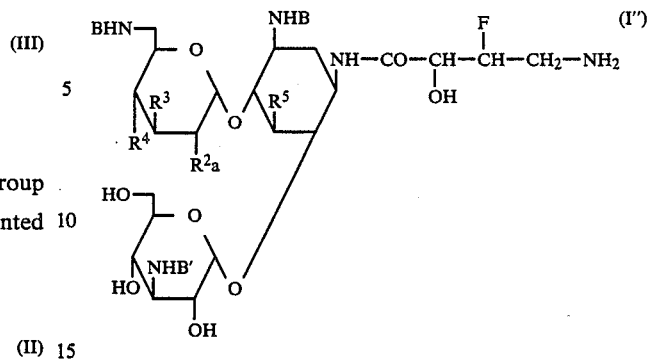

(I'')

wherein $R^2a$, $R^3$, $R^4$, $R^5$, B and B' have the same meaning as defined above, contains any remaining amino-protecting groups (B,B'), (iii) removing the amino-protecting groups from the reduction product of the formula (II'').

In the above-described process for the production of the compounds of this invention, conventional amino-protecting group or groups may be used as the amino-protecting group or groups for protecting all or some of the amino groups other than the 1-amino group of the starting compound of the general formula (II). The available amino-protecting groups may include monovalent amino-protecting groups, for example, alkoxycarbonyl groups such as tert-butoxycarbonyl and tert-amyloxycarbonyl; cycloalkyloxycarbonyl groups such as cyclohexyloxycarbonyl; aralkyloxycarbonyl groups such as benzyloxycarbonyl; hydrolytically-cleavable, substituted lower alkanoyl groups such as trifluoroacetyl and o-nitrophenoxyacetyl; phosphinothioyl groups such as diphenylphosphinothioyl and dimethylphosphinothioyl; and phosphinyl groups such as diphenylphosphinyl. Further, phthaloyl may be used as a divalent amino-protecting group. On the other hand, the amino groups other than the 1-amino group of the starting compound of the formula (I) may also be protected by converting it into the form of a Schiff base. The introduction of these amino-protecting groups may be carried out in a manner known per se in the synthesis of peptides or the like, for example, by using an appropriate reagent known for the introduction of amino-protecting group or groups, which may be in the form of an acylating agent such as acid halide, acid azide, active ester, acid anhydride or the like. By using such a reagent at a molar equivalent ratio within a range of 0.5–6, various partially amino-protected derivatives can be produced at a desired ratio owing to differences in the reactivity among the individual amino groups of the starting compound (II).

In the above-described process for the production of the compounds of the formula (I') according to this invention, such an amino-protected derivative of the starting compound of the formula (II) of which all or some of the amino groups other than the 1-amino group have been protected, for example, 3,2',6',3''-tetra-N-protected derivative, 3,2',6'-tri-N-protected derivative, 3,6'- or 6',3''-di-N-protected derivative, or 6'-mono-N-protected derivative may be employed. Further, a mixture of these partially amino-protected derivatives may also be used for the acylation of the 1-amino group of the starting compound (II).

In order to produce the desired compound of the formula (I') in a high yield by the process described above, essentially it only needs to acylate the 1-amino group of the starting compound of the formula (II) selectively with (2R,3R)-4-azido-3-fluoro-2-hydroxybutyric acid of the formula (III). Therefore, it will apparently be most preferable to use, as a starting material for the above process, such a protected derivative of the starting compound of the formula (II) of which all amino groups other than the 1-amino group have been blocked with amino-protecting groups.

The following method may be used, by way of example, for preparing such protected derivative of the compound of the general formula (II) of which all amino groups other than the 1-amino group have been protected. A 3,6'-di-N-protected derivative or 3,2',6'-tri-N-protected derivative of the starting compound (II) is formed, first of all, in a high yield by making use of the N-protecting method of Japanese patent application first publication "kokai" No. 153944/77 (or U.S. Pat. No. 4,136,254) or Japanese patent application first publication "kokai" No. 64598/80 (or claim 1 of U.S. Pat. No. 4,297,485), namely, by reacting a kanamycin compound of the formula (II) with cations of a divalent transition metal, such as copper (II), nickel(II), cobalt-(II) or zinc cations to form a metal complex, then reacting a reagent for the introduction of amino-protecting groups, with the metal complex so as to protect all the amino groups other than the two, 1- and 3"-amino groups of the kanamycin moiety of the complex (which have been blocked owing to complexing with the divalent metal cation) with the amino-protecting groups respectively, and then removing the divalent metal cation from the complex, for example, through its treatment with a cation exchange resin, hydrogen sulfide or aqueous ammonia. A tri-N-protected derivative or tetra-N-protected derivative of the starting compound (II), of which all amino groups other than the 1-amino group of the compound (II) have been protected, can thereafter be prepared in high yield by using such process as developed by the present inventors for the production of such a protected derivative of kanamycins whose all the amino groups other than the 1-aminogroup have been protected selectively, which process is described Japanese patent application first publication "kokai" No. 164696/1980 or claim 15 of U.S. Pat. No. 4,297,485. In the process of claim 15 of U.S. Pat. No. 4,297,485 a formic acid ester, di-or trihalogenoalkanoic acid ester, preferably, ethyl trifluoroacetate, or N-formylimidazole is reacted with such as amino-protected derivative of an aminoglycosidic antibiotic, of which all amino groups other than the 1-amino and 3"-amino groups have been protected, to perform the selective acylation of the 3"-amino group, whereby the 3"-amino group of the N-protected aminoglycosidic antibiotic derivative can be protected selectively with the formyl or di- or tri-haloaklanoyl group without acylating the 1-amino group.

In the above-described process for the production of the compounds of this invention, the 1-N-acylating reaction, by which the 1-amino group of the starting compound (II) or its partially amino-protected derivative is acylated with (2R,3R)-4-azido-3-fluoro-2-hydroxybutyric acid of formula (III), can be carried out by reacting with (2R,3R)-4-azido-3-fluoro-2-hydroxybutyric acid of the formula (III) or its reactive derivative (functional equivalent) according to the conventional dicyclohexylcarbodiimide technique, mixed acid anhydride technique, azid technique, active ester technique or the like. The reaction temperature may suitable be in a range of 0° C. to 30° C. The amino-protecting group or groups present in the N-protected derivative of the starting compound of formula (II) may preferably be tertbutoxycarbonyl or p-methoxybenzyloxycarbonyl groups, so that the removal of the amino-protecting group from said N-protected derivative can be easily achieved by treating same in an aqueous solution of trifluoroacetic acid or acetic acid or in a dilute aqueous solution of hydrochloric acid. Benzyloxycarbonyl is also a convenient amino-protecting group, because it can be cleaved readily by conducting usual catalytic reduction in the presence of a platinum group catalyst such as palladium or platinum oxide.

In the process of this invention described above, the 1-N-acylating reaction may preferably be conducted according to the active ester technique in an aqueous organic solvent. An active ester, which may be prepared in a usual manner, is the N-hydroxysuccinimide of (2R,3R)-4-azido-3-fluoro-2-hydroxybutyric acid, and this active ester compound may be used in an amount of 1-3 molar proportions, preferably, 1-1.5 molar proportions, for instance, when the N-hydroxysuccinic imide is reacted with the compound of the formula (II). A water-miscible organic solvent such as dioxane, dimethoxyethane, dimethylformamide, tetrahydrofuran or triethylamine may be used as a preferable solvent for the 1-N-acylation.

The terminal azido group ($-N^3$) of the 1-N-acyl group of the 1-N-acylated reaction product compound of the formula (IV) thus prepared is then converted into an amino group ($-NH_2$) by its reduction. This reduction can be carried out catalytically by a usual method for reduction of azido groups.

Where the reduction reaction product of the formula (I") so obtained still contains the remaining amino-protecting groups (B, B'), these amino-protecting groups are then removed. This removal may be carried out by a usual deprotection method. Namely, the amino-protecting groups of the above-described alkyloxycarbonyl type may be removed by treating the reduction product (I") in an aqueous solution of trifluoroacetic acid, acetic acid or the like or in a dilute aqueous solution of hydrochloric acid or the like. Where the amino-protecting groups of the amino-protected derivative of the starting compound of the formula (II) are aralkyloxycarbonyl groups such as benzyloxycarbonyl groups, it is unnecessary to conduct any additional step to remove the amino-protecting groups, since they can be removed already in the preceding catalytic reduction (hydrogenolysis) step. Where phthaloyl groups are the remaining amino-protecting groups, they can be removed by heating the reduction product (I") in an alcoholic solution of hydrazine hydrate.

(2R,3R)-4-Azido-3-fluoro-2-hydroxybutyric acid of the formula (III) is a novel compound which has now been synthesized by the present inventors. A description will next be made of a method for synthesizing this compound from known compound, i.e., 3-deoxy-3-fluoro-1,2-0-isopropylidene-α-D-glucofuranose {this compound described in Japanese patent application first publication "Kokai" No. 40297/86}.

First of all, 3-deoxy-3-fluoro-1,2-0-isopropylidene-α-D-glucofuranose {hereinafter called "Compound (1)" of the following formula:

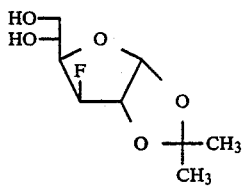

oxidized with sodium metaperiodate (NaIO₄) to form a 4-formyl compound of the following formula:

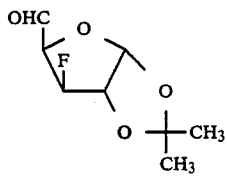

namely, 3-deoxy-3-fluoro-5-aldo-1,2-0-isopropylidene-α-D-xylofuranose which; will hereinafter be called "Compound (2)" together with formaldehyde {see Referential Example 1(a) given hereinafter}. The 4-formyl group of the compound (2) is then oxidized with silver nitrate to form 3-deoxy-3-fluoro-1,2-0-isopropylidene-α-D-xylofuranuronic acid {hereinafter called "Compound (3)"} of the following formula:

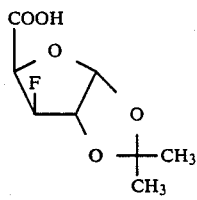

}see Referential Example 1(a)}. When diazomethane (CH₂N₂) is reacted with the 4-carboxylic residue of Compound (4) to esterify same, there is formed methyl 3-deoxy-3-fluoro-1,2-0-isopropylidene-α-D-xylofuranuronate }hereinafter called "Compound (4)"} of the following formula:

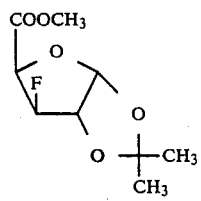

{see Referential Example 1(b) given hereinafter}.

Upon hydrolysis of Compound (4) under acidic conditions, for example, by using an aqueous solution of trifluoroacetic acid, the 1,2-0-isopropylidene group is removed from Compound (4) to form methyl 3-deoxy-3-fluro-D-xylofuranuronate {hereinafter called "Compound (5)"} of the following formula:

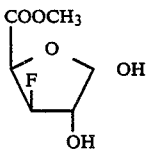

{see Referential Example 1(c) given hereinafter}. Upon oxidation of Compound (5) with sodium metaperiodate, there are formed formic acid (HCOOH) and methyl (2R,3S)-3-formyl-3-fluoro-2-hydroxypropionate {hereinafter called "Compound (6)"} of the following formula:

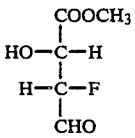

{see Referential Example 1(d)}. Subsequent reduction of the aldehyde group of Compound (6) with sodium boro-hydride (NaBH₄) yields methyl (2R,3R)-3-fluoro-2,4-dihydroxybutyrate {hereinafter called "Compound (8)"} of the following formula:

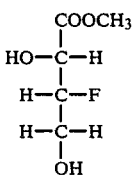

{see Referential Example 1(d)}. Alkaline hydrolysis also takes place at the same time, so that (2R,3R)-3-fluoro-2,4-dihydroxybutyric acid {hereinafter called "Compound (7)"} of the following formula:

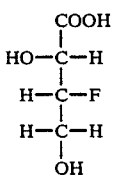

is by-formed in a small amount. Compound (7) is therefore reacted with diazomethane (CH₂N₂) for its esterification, whereby its corresponding methyl (2R,3R)-3-fluoro-2,4-dihydroxybutyrate {hereinafter called "Compound (8)"} is formed {see Referential Example 1(d)}.

When α,α-dimethoxytoluene of the following formula:

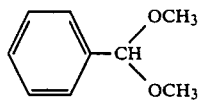

is reacted with the 2- and 4-hydroxyl groups of Compound (8) in the presence of p-toluenesulfonic acid as an acidic catalyst, there is formed methyl (2R,3R)-2-4-0-benzylidene-3-fluoro-2,4-dihydroxybutyrate hereinafter called "Compound (9)" of the following formula:

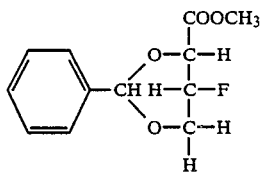

{see Referential Example 1(e)}.

When N-bromosuccinimide is reacted further with Compound (9) in the presence of barium carbonate (BaCO₃) as a dehydrobromination agent (by "Hanessian" process), there is formed methyl (2R,3S)-2-benzoyloxy-4-bromo-3-fluorobutyrate {hereinafter called "Compound (10)"} of the following formula:

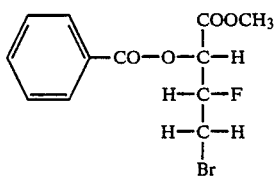

{see Referential Example 1(f)}. Upon hydrolysis of Compound (10) with an aqueous acetic acid solution containing 20% hydrogen bromide for the debenzoylation, i.e., removal of the 2-0-benzoyl group of Compound (10), (2R,3S)-4-bromo-3-fluoro-2-hydroxybutyric acid {hereinafter called "Compound (11)"} of the following formula:

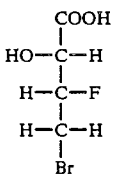

is formed {see Referential Example 1(g)}. Treatment of Compound (11) with diazomethane provides its corresponding methyl ester {hereinafter called "Compound (12)"}. When the 4-bromo group of Compound (12) is reacted with sodium azide (NaN₃) in dry dimethylformamide (DMF) to convert Compound (12) into an azido derivative, there is formed methyl (2R,3R)-4-azido-3-fluoro-2-hydroxybutyrate {hereinafter called "Compound (13)"} of the following formula:

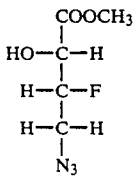

{see Referential Example 1(g)}. Upon alkaline hydrolysis of Compound (13) with an aqueous solution of sodium hydroxide, its corresponding (2R,3R)-4-azido-3-fluoro-2-hydroxybutyric acid {hereinafter called "Compound (14)"} is obtained {see Referential Example 1(h)}. When Compound (14) is reacted with dicyclohexylcarbodiimide and N-hydroxysuccinimide in order to form an active ester of Compound (14), the N-hydroxy succinimide ester of (2R,3R)-4-azido-3-fluoro-2-hydroxybutyric acid {hereinafter called "Compound (15)"} is formed {see Referential Example 1(i)}.

On the other hand, 2',3'-dideoxy-2'-fluorokanamycin A useful as a starting material for the production of the compounds of this invention is a novel compound. Production of this compound is described in the specifications of Japanese patent application first publication "Kokai" No. 93296/87 and U.S. Pat. No. 4,661,474 as assigned commonly to the present assignee, of which descriptions are hereby incorporated herein for reference. In addition, 5-deoxy-5-fluorokanamycin B, 5,3'-dideoxy-5-fluorokanamycin B and 5,3',4'-trideoxy-5-fluorokanamycin B which may be used similarly as starting materials are also novel compounds. Production of these compounds is described in the specifications of Japanese patent application No. 181850/86 European patent application Publication No. 0259014, and U.S. patent application Ser. No. 078,996 as assigned commonly to the present assignee, of which descriptions are hereby incorporated herein for reference.

This invention will next be illustrated with reference to Referential Example 1 which will demonstrate the production of (2R,3R)-4-azido-3-fluoro-2-hydroxybutyric acid and its active ester, and with reference to Examples 1–10 which will show the production of the exemplary compounds of this invention.

REFERENTIAL EXAMPLE 1

(a) Synthesis of 3-deoxy-3-fluoro-1,2-0-isopropylidene-α-D-xylofuranuronic acid {Compound (3)} from 3-deoxy-3-fluoro-1,2-0-isopropylidene-α-D-glucofuranose {Compound (1)}

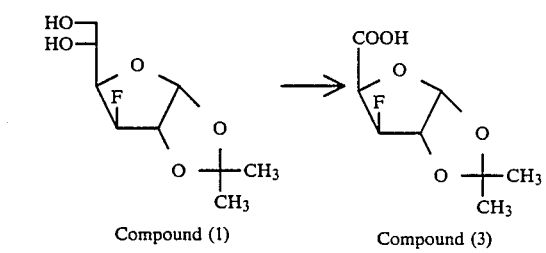

3-Deoxy-3-fluoro-1,2-0-isopropylidene-α-D-glucofuranose {Compound (1); this compound is described in Japanese patent application first publication "Kokai" No. 40297/86} (8.3 g) was dissolved in water (120 ml). Sodium metaperiodate (8.0 g) was added to the resultant aqueous solution, followed by subjecting the mixture to an oxidative reaction for 0.5 hour at room temperature. The reaction mixture was extracted with ethyl acetate (500 ml×2), and the resulting ethyl acetate solution was washed with a 10% aqueous solution of sodium sulfate (100 ml×2), dried over anhydrous sodium sulfate and then concentrated to obtain the 4-formyl compound {Compound (2)} as a syrup (6.53g). The syrup and silver nitrate (12.3 g) were thereafter dissolved in water (65 ml), followed by addition of an aqueous solution (65 ml) of potassium hydroxide (8.1 g). The resultant mixture was stirred for 0.5 hour. The oxidative reaction futher took place. The reaction mixture was filtered, followed by addition of 6N hydrochloric acid (20 ml) to the resulting filtrate, and the aqueous solution layer was washed with chloroform (900 ml×6). The chloroform solution thus obtained was dried over anhydrous sodium sulfate and then concentrated to afford the titled Compound (3) as colorless crystals (6.58 g). Yield: 86%.

m.p. 131°-132° C.

$[\alpha]_D^{22}$ −52° (c 1, chloroform)

(b) Synthesis of methyl 3-deoxy-3-fluoro-1,2-0-isopropylidene-α-D-xylofuranuronate {Compound (4)}

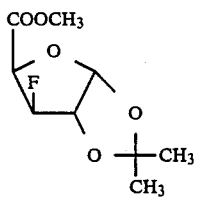

Compound (4)

Compound (3) (6.0 g) obtained in the preceding step (a) was dissolved in diethyl ether (120 ml), followed by addition of a solution of diazomethane in diethyl ether until the reaction mixture presented a pale yellow color. A reaction of methyl esterification took place. The reaction mixture was then concentrated to afford the titled Compound (4) as colorless crystals (6.31 g). Yield: 98% m.p. 71°-72° C.

$[\alpha]_D^{22}$ −45° (c 1, chloroform)

(c) Synthesis of methyl 3-deoxy-3-fluoro-D-xylofuranuronate {Compound (5)}

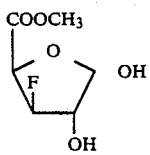

Compound (5)

Compound (4) (290 mg) obtained in the above step (b) was dissolved in a mixture (3 ml) of trifluoroacetic acid and water (9:1), followed by a reaction for 4 hours at room temperature. De-isopropylidenation reaction took place. The reaction mixture was concentrated, and the resultant syrup was purified by chromatography on a silica gel column (developer: mixed solvent of ethyl acetate and toluene, 2:1), thereby giving the titled Compound (5) as a colorless syrup (213 g). Yield: 90%. Upon reprecipitation of the reaction product from a mixed solvent of ethyl acetate and hexane, needle-like crystals were obtained. m.p. 80°-81° C.

(d) Synthesis of methyl (2R,3R)-3-fluoro-2,4-dihydroxybutyrate {Compound (8)}

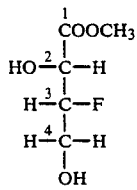

Compound (8)

Compound (5) (1 g) obtained in the preceding step (c) was dissolved in water (15 ml), in which sodium metaperiodate (1.3 g) was dissolved to conduct an oxidative reaction overnight (for 19 hours) at room temperature. The reaction mixture was extracted with ethyl acetate (100 ml×5). The resultant ethyl acetate solution was dried over anhydrous sodium sulfate and then concentrated, thereby yielding the aldehyde compound {Compound (6)} of the following formula:

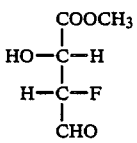

as a syrup (798 mg).

The syrup was thereafter dissolved in methanol (16 ml). To the resultant solution, sodium borohydride (300 mg) was gradually added (in five 60-mg portions at intervals of 0.5 hour) to conduct a reduction reaction. Thereafter, 1 N hydrochloric acid was added under ice cooling to make the reaction mixture acidic (pH 1). The reaction mixture was then concentrated and the residue was extracted with tetrahydrofuran. A tetrahydrofuran extract containing Compound (8) and a small amount of a reaction product {Compound (7)} represented by the formula:

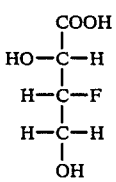

was treated with a dietyl ether solution of diazomethane in the same manner as in the above step (b) so as to convert the reaction product into its methyl ester. A syrup, which had been obtained by concentrating the tetrahydrofuran extract thus-treated was purified by chromatography on a silica gel column (developer: ethyl acetate) to obtain the titled Compound (8) as colorless needle-like crystals (625 mg). Yield: 74% m.p. 89°-90° C.

$[\alpha]_D^{22}$ −2° (c 1, methanol)

$^1$H-NMR spectrum (in methanol-d$_4$; internal standard: TMS):

δ 3.79 (3H, s. COOCH$_3$), 4.38 (1H, dd, H-2), 4.80 (1H, dddd, H-3).

$J_{H\text{-}2,H\text{-}3}$=2.3, $J_{H\text{-}2,F}$=30.0, $J_{H\text{-}3,F}$=47.5 Hz.

(e) Synthesis of methyl (2R,3R)-2,4-0-benzylidene-3-fluoro-2,4-dihydroxybutyrate {Compound (9)}

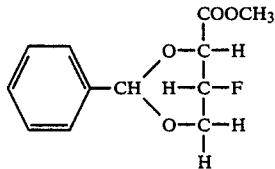

Compound (8) (885 mg) obtained in the preceding step (d) and p-toluenesulfonic acid (200 mg) were dissolved in dry DMF (18 ml), followed by addition of α,α-dimethoxytoluene {C$_6$H$_5$-CH-(OCH$_3$)$_2$} (2.65 ml). The reaction was effected at 50° C. for 1 hour under a reduced pressure of 15 mmHg.

A 5% aqueous solution of sodium hydrogencarbonate (4 ml) was added to the reaction mixture. Subsequent to neutralization, the reaction mixture was concentrated. The residue was extracted with chloroform. After washing the resultant chloroform solution with water, it was dried over anhydrous sodium sulfate and then concentrated to give a crude product of the titled Compound (9) as pale yellow crystals (1.26 g) (yield of the crude product: 91%).

The crude Compound (9) was recrystallized from a mixed solvent of benzene and n-hexane to obtain Compound (9) as colorless acicular crystals (993 mg). Yield: 71%.

m.p. 107.5°–108.5° C.

$[\alpha]_D^{22}$ −45° (c 1, chloroform)

(f) Synthesis of methyl (2R,3S)-2-benzoyloxy-4-bromo-3-fluorobutyrate {Compound (10)}

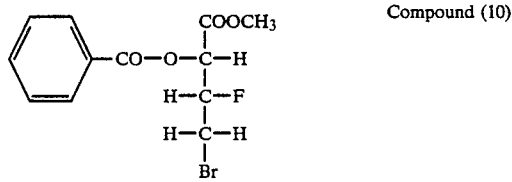

Compound (10)

Compound (9) (340 mg) obtained in the preceding step (e), barium carbonate (460 mg) and N-bromosuccinimide (280 mg) were suspended in carbon tetrachloride (7 ml), and the resultant mixture was heated under reflux for 1 hour. Bromination by the Hanessian process took place.

The reaction mixture was concentrated and the residue was extracted with toluene. After washing the toluene solution with water, it was dried over anhydrous sodium sulfate and then concentrated to obtain a syrup. The syrup was purified by chromatography on a silica gel column (developer: mixed solvent of toluene and ethyl acetate, 12:1), thereby affording the titled Compound (10) as colorless crystals (388 mg). Yield: 86%.

m.p. 67°–68° C.

$[\alpha]_D^{22}$ −16° (c 1, chloroform)

(g) Synthesis of methyl (2R,3R)-4-azido-3-fluoro-2-hydroxybutyrate {Compound (13)}

Compound (13)

To Compound (10) (65 mg) obtained in the preceding step (f), were added water (0.32 ml) and a 30% solution (0.64 ml) of hydrogen bromide in acetic acid. The resulting mixture was stirred at 90° C. for 8 hours. A de-benzoylation reaction took place and at the same time, the ester was converted into its corresponding acid. The reaction mixture, which contained a reaction product {Compound (11)} represented by the following formula:

and had become homogeneous, was concentrated and the residue was dissolved in tetrahydrofuran (2 ml). The reaction product was then converted into its methyl ester by reacting with a diethyl ether solution of diazomethane in the same manner as in the above step (b). After concentration, there was obtained a syrup (54 mg) which contained the methyl ester {Compound (12)}. The syrup was dissolved in dry DMF (1.1 ml), followed by addition of sodium azide (24.5 mg). The resultant mixture was heated at 80° C. for 50 minutes under stirring (for the azidation).

The reaction solution containing the titled Compound (13) so formed was concentrated and the resultant syrup was extracted with ethyl acetate. The ethyl acetate solution was washed with water, dried over anhydrous sodium sulfate and then concentrated. The syrup obtained was purified by chromatography on a silica gel column (developer: mixed solvent of toluene and ethyl acetate, 10:1), thereby yielding the titled Compound (13) as a colorless syrup (30.7 mg). Yield: 85%.

Infrared absorption spectrum: 2110 cm$^{-1}$ (N$_3$)

$[\alpha]_D^{17.5}$ −22° (c 0.5, chloroform)

(h) Production of (2R,3R)-4-azido-3-fluoro-2-hydroxybutyric acid {Compound (14)}

Compound (14)

Compound (13) (90 mg) obtained in the preceding step (g) was dissolved in methanol (1.8 ml), followed by addition of a 0.6 N aqueous solution (1.8 ml) of sodium hydroxide. The reaction was effected at room temperature for 0.5 hour to hydrolyze the former compound. The reaction mixture was concentrated, and when it became syrup, water (10 ml) was added thereto, followed by further addition of a small amount of 1 N hydrochloric acid under ice cooling so as to make the aqueous solution acidic (pH 2). The aqueous solution was extracted with ethyl acetate. The resulting ethyl acetate solution was dried over anhydrous sodium sulfate and then concentrated. The titled Compound (14) was obtained as a colorless syrup (71.3 mg). Yield: 86%.

$[\alpha]_D^{18}$ −22° (c 0.5, methanol)

Infrared absorption spectrum: 2110 cm$^{-1}$ $^1$H-NMR spectrum (in methanol-d$_4$; internal standard: TMS):

δ 3.49 (1H, dddd, H-4a), 3.72 (1H, dt, H-4b), 4.25 (1H, dd, H-2), 4.92 (1H, dddd, H-3), $J_{H-2,f}$=3.10, Jhd H-3,F=48.0, $J_{H-2,H-3}$=2 Hz.

(i) Production of the N-hydroxysuccinimide ester of (2R,3R)-4-azido-3-fluoro-2-hydroxybutyric acid {Compound (15)}

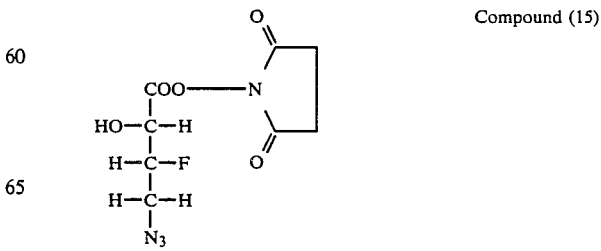

Compound (15)

Compound (14) (48 mg) of the preceding step (h) and N-hydroxysuccinimide (34 mg) were dissolved in dry ethyl acetate (2 ml), to which dicyclohexylcarbodiimide (63 mg) was added under stirring. The mixture obtained was stirred at room temperature for 1 hour (for the conversion into an active ester).

The while suspension obtained was filtered and an insoluble matter was washed with dry ethyl acetate. The filtrate and washing were combined together and concentrated to give the titled Compound (15) as a pale yellow syrup (76 mg).

Infrared absorption spectrum: 2110 cm$^{-1}$ (N$^3$)

$^1$H-NMR spectrum (in chloroform-d; internal standard: TMS):

δ 3.61 (1H, ddd, H-4a), 3.82 (1H, dt, H-4b), 4.74 (1H, dd, H-2), 5.02 (1H, dddd, H-3).

$J_{H-2,H-3}=2.2$, $J_{-2,F}=25.5$, $J_{H-3,F}=46.5$ Hz.

EXAMPLE 1

(1) Preparation of 1-N-{(2R,3R)-4-azido-3-fluoro-2-hydroxybutyryl}-3,6'-bis{N-benzyloxycarbonyl}-3"-N-trifluoroacetylkanamycin A {Compound (17)}

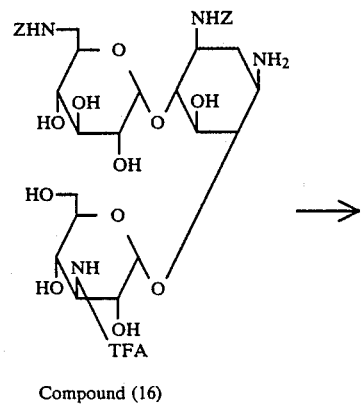

Compound (16)

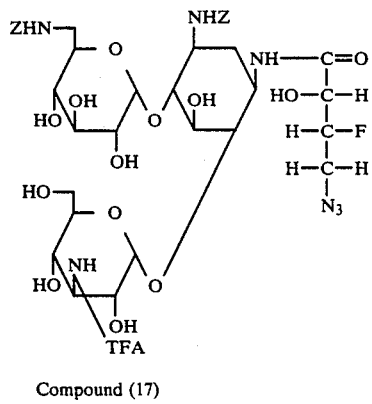

Compound (17)

wherein TFA means a trifluoroacetyl group and Z denotes a benzyloxycarbonyl group, and TFA and Z will have the same meaning hereinafter.

Compound (16) represented by the above formula, namely, 3,6'-bis-N-(benzyloxycarbonyl)-3"-trifluoroacetylkanamycin A {the compound described in Example 33 of U.S. Pat. No. 4,297,485} (150 mg) and sodium carbonate (18.7 mg) were dissolved in a mixed solvent (4 ml) of tetrahydrofuran and water (1:1). The resultant solution was added with a solution which had been prepared by dissolving in tetrahydrofuran (2 ml) Compound (15) (82 mg) as obtained in Referential Example 1(i) above. The reaction was made at room temperature for 10 minutes. The reaction mixture was concentrated and the residue was washed successively with water and diethyl ether. The titled Compound (17) was obtained as a colorless solid (128.5 mg). Yield: 73%.

(2) Production of 1-N-{(2R,3R)-4-amino-3-fluoro-2-hydroxybutyryl}kanamycin A (Invention Compound No. 1)

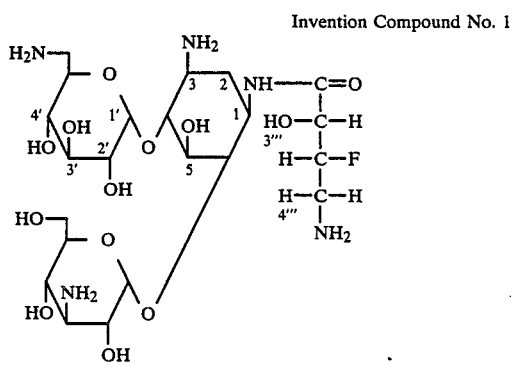

Invention Compound No. 1

Compound (17) (88.5 mg) obtained in the preceding step (1) was dissolved in a liquid mixture (8 ml) of 2 N aqueous ammonia and tetrahydrofuran (1:1). The reaction was conducted overnight at room temperature to remove the 3"-N-trifluoroacetyl group from Compound (17). A solid product, which had been obtained by concentrating the reaction mixture, was dissolved in a liquid mixture (4.2 ml) of acetic acid, dioxane and water (1:10:10). Into the resultant solution, hydrogen gas was blown at room temperature in the presence of palladium black as a catalyst, whereby the reaction product was catalytically reduced for 1 hour to convert the azido group into an amino group and also to remove the N-benzyloxycarbonyl group. After filtration of the reaction mixture, the resultant filtrate was concentrated. A solid product so obtained was dissolved in water. The resultant solution was caused to pass through a column of "CM-Sephadex C-25" (trade name) (18 ml). The column was developed gradiently with aqueous ammonia while gradually increasing the concentration of ammonia from 0N to 0.5N. The eluate fractions (40–50 ml) were collected, which were found to contain the intended compound as tested by the ninhydrin reaction. The fractions were concentrated to obtain the titled Invention Compound No. 1 as a colorless solid (47.0 mg).

$[\alpha]_D^{24}$ +82° (c 0.5, water)

$^1$H-NMR spectrum (in 20% ND$_3$-D$_2$O internal standard: TMS):

δ 4.24 (1H, dd, H-2'''), 4.86 (1H, dddd, H-2'''), 5.12 (1H, d, H-1''), 5.29 (1H, d, H-1').

$J_{H-1',H-2'}=3.8$, $J_{H-1'', H-2''}=3.8$, $J_{H-2''',F}=31$, $J_{H-3''',F}=47.5$, $J_{H-2''',H-3'''}$ 2 Hz.

EXAMPLE 2

(1) Preparation of 1-N-{(2R,3R)-4-azido-3-fluoro-2-hydroxybutyryl}-3,6'-bis(N-benzyloxycarbonyl)-2,3'-dideoxy-3"-N-trifluoroacetylkanamycin A {Compound (18)}

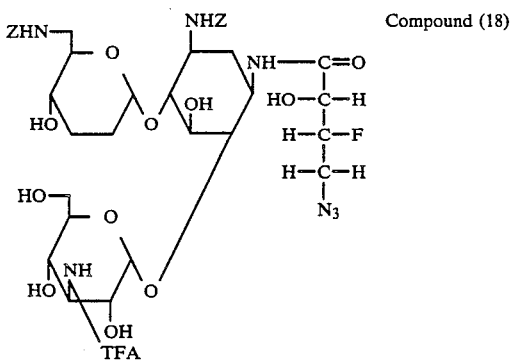

Compound (18)

3,6'-Bis(N-benzyloxycarbonyl)-2',3'-dideoxy-3"-N-trifluoroacetylkanamycin A {see Japanese patent application first publication "Kokai" No. 41692/85 or U.S. Pat. No. 4,547,492} (94 mg) and sodium carbonate (12 mg) were dissolved in a mixed solvent (2 ml) of tetrahydrofuran and water (1:1). The resultant solution was added with a solution which had been obtained by dissolving in tetrahydrofuran (1 ml) Compound (15) (43 mg) as prepared in Referential Example 1(i) above. The reaction was effected at room temperature for 10 minutes. The reaction mixture was concentrated and the residue was washed successively with water and diethyl ether to yield the titled Compound (18) (102.5 mg). Yield: 93%.

(2) Production of 1-N-{(2R,3R)-4-amino3-fluoro-2-hydroxybutyryl}2',3'-dideoxykanamycin A (Invention Compound No. 2)

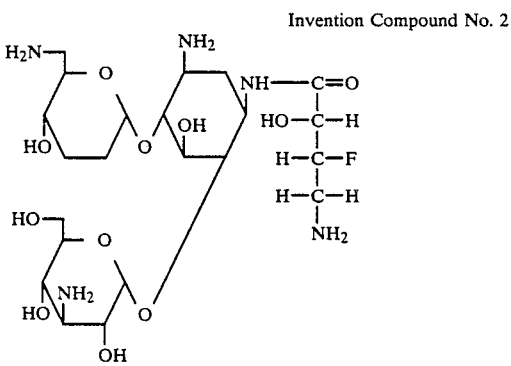

Invention Compound No. 2

Compound (18) (86 mg) obtained in the preceding step (1) was dissolved in a liquid mixture (8 ml) of 2 N aqueous ammonia and tetrahydrofuran (1:1). The compound was subjected to a hydrolytic reaction at room temperature overnight to remove the 3"-N-trifluoroacetyl group. A solid which had been obtained by concentrating the reaction mixture, was dissolved in a liquid mixture (4.2 ml) of acetic acid, dioxane and water (1:10:10). Into the resulting solution was blown hydrogen gas at room temperature in the presence of palladium black as a catalyst, whereby the reaction product was catalytically reduced for 1 hour to convert the azido group into an amino group and also to remove the N-benzyloxycarbonyl group. After filtration of the reaction mixture, the resultant filtrate was concentrated. A solid product obtained was dissolved in water. The resultant solution was caused to pass through a column of "CM-Sephadex C-25" (trade name) (15 ml). The column was developed gradiently with aqueous ammonia while gradually increasing the concentration of ammonia from 0N to 0.5N. Collected were eluate fractions (35–45 ml) which were found to contain the intended compound as tested by the ninhydrin reaction. The fractions were concentrated to obtain the titled Invention Compound No. 2 as a colorless solid (42.6 mg).

$[\alpha]_D^{24}$ +85° (c 0.5, water)

EXAMPLE 3

(1) Preparation of 1-N-{(2R,3R)-4-azido-3-fluoro-2-hydroxybutyryl}-3,6'-bis(N-benzyloxycarbonyl)-2',3'-dideoxy-2'-fluoro-3"-N-trifluoroacetylkanamycin A {Compound (19)}

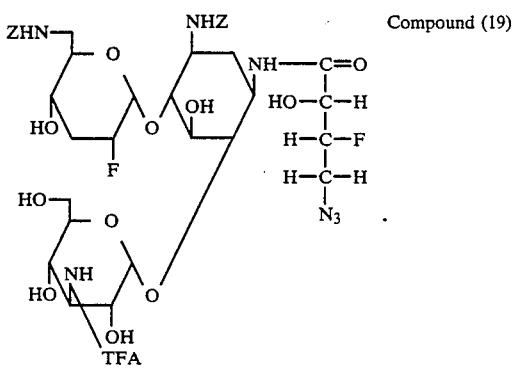

Compound (19)

3,6'-Bis(N-benzyloxycarbonyl)-2',3'-dideoxy-2'-fluoro-3"-N-trifluoroacetylkanamycin A {see Japanese patent application first publication "Kokai" No. 231027/85} (95 mg) and sodium carbonate (12 mg) were dissolved in a mixed solvent (2 ml) of tetrahydrofuran and water (1:1). The resultant solution was added with a solution which had been obtained by dissolving in tetrahydrofuran (1 ml) Compound (15) (45 mg) as prepared in Referential Example 1(i) above. The reaction was effected at room temperature for 10 minutes. The reaction mixture was concentrated and the residue was washed successively with water and diethyl ether to obtain the titled Compound (19) (100.7 mg).

(2) Production of 1-N-{(2R,3R)-4-amino-3-fluoro-2-hydroxybutyryl}2',3'-dideoxy-2'-flurokanamycin A (Invention Compound No. 3)

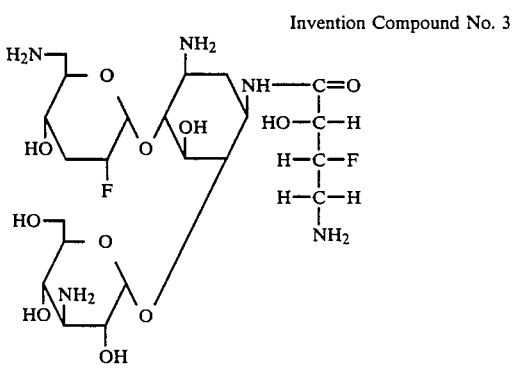

Invention Compound No. 3

Compound (19) (85 mg) obtained in the preceding step (1) was dissolved in a liquid mixture (8 ml) of 2N aqueous ammonia and tetrahydrofuran (1:1). The compound was subjected to a hydrolytic reaction overnight at room temperature to remove the 3"-N-trifluoroacetyl group. A solid product, which had been obtained by concentrating the reaction mixture, was dissolved in a liquid mixture (4.2 ml) of acetic acid, dioxane and water (1:10:10). Into the resulting solution was blown hydrogen gas at room temperature in the presence of palladium black as a catalyst, whereby the reaction product was catalytically reduced for 1 hour to convert the azido group into an amino group and also to remove the N-benzyloxycarbonyl group. After filtration of the reaction mixture, the resultant filtrate was concentrated. A solid product obtained was dissolved in water. The resultant solution was caused to pass through a column of "CM-Sephadex C-25" (trade name) (15 ml). The column was developed gradiently with aqueous ammonia while gradually increading the concentration of ammonia from 0N to 0.2N. The eluate fractions (45–60 ml) were collected, which were found to contain the intended compound as tested by the ninhydrin reaction. The fractions were concentrated to afford the titled Invention Compound No. 3 as a colorless solid (43.7 mg).

$[\alpha]_D^{24}$ +82° (c 0.5, water)

EXAMPLE 4

(1) Preparation of 1-N-{(2R,3R)-4-azido-3-fluoro-2-hydroxybutyryl}-3,6-bis(N-benzyloxycarbonyl-5-deoxy-5-fluoro-3″-trifluoroacetylkanamycin A {Compound (21)}

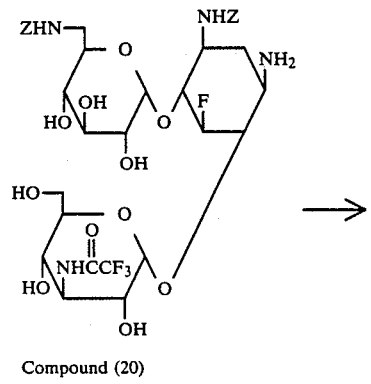

Compound (20)

Compound (21)

Compound (20) of the above formula, namely, 3,6′-bis(N-benzyloxycarbonyl)-5-deoxy-5-fluoro-3″-N-trifluoroacetylkanamycin A {which had been prepared by protecting 5-deoxy-5-fluorokanamycin A in the same manner as in Examples 1 and 33 of U.S. Pat. No. 4,297,485} (112 mg) was dissolved in a 1:1 mixed solvent (4.5 ml) of tetrahydrofuran and water. The resultant solution was added with a solution which had been obtained by dissolving in tetrahydrofuran (2 ml) Compound (15) (74 mg) as prepared in Referential Example 1(i) above. The reaction was effected at room temperature for 10 minutes. A 5% aqueous solution of sodium hydrogencarbonate (0.45 ml) was added to the reaction mixture to neutralize same, followed by addition of a tetrahydrofuran solution of Compound (15) in the same amount as added above. After the reaction for 10 minutes, a 5% aqueous solution of sodium hydrogencarbonate (1.3 ml) was added similarly as above. The reaction mixture was concentrated and the residue was washed successively with water and diethyl ether to obtain the titled Compound (21) (121 mg).

(2) Production of 1-N-{(2R,3R)-4-amino-3-fluoro-2-hydroxybutyryl}-5-deoxy-5-fluorokanamycin A (Invention Compound No. 4)

Invention Compound No. 4

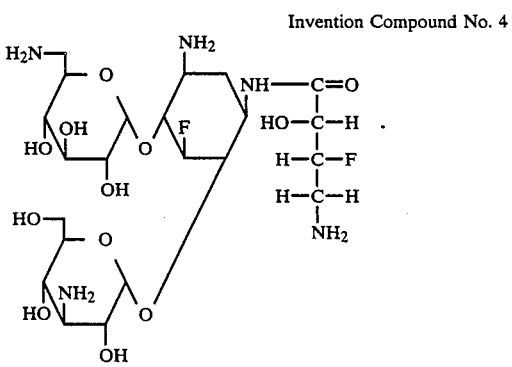

Compound (21) (119 mg) obtained in the preceding step (1) was dissolved in a liquid mixture (6 ml) of 2N aqueous ammonia and tetrahydrofuran (1:1). The compound was subjected to a hydrolytic reaction for 24 hours at room temperature to remove the 3″-N-trifluoroacetyl group. The reaction mixture was then concentrated. A solid product obtained was dissolved in a liquid mixture (4.9 ml) of acetic acid, dioxane and water (1:20:20). Into the resultant solution was blown hydrogen gas at room temperature in the presence of palladium black as a catalyst, whereby the reaction product was catalytically reduced for 2 hours to convert the azido group into an amino group and also to remove the N-benzyloxycarbonyl group. After filtration of the reaction mixture, the resultant filtrate was concentrated. A solid product obtained was dissolved in water. The resultant solution was caused to pass through a column of "CM-Sephadex C-25" (trade name). The column was developed gradiently with aqueous ammonia while gradually increasing the concentration of ammonia from 0N to 0.2N. Eluate fractions containing the intended compound of this invention were collected and then concentrated to afford the titled Invention Compound No. 4.

$[\alpha]_D^{24}$ +81° (c 0.5, water)

EXAMPLE 5

(1) Preparation of 1-N-{(2R,3R)-4-azido-3-fluoro-2-hydroxybutyryl}-3,2′,6′-tris(N-benzyloxycarbonyl)-3″-N-trifluoroacetylkanamycin A {Compound (22)}

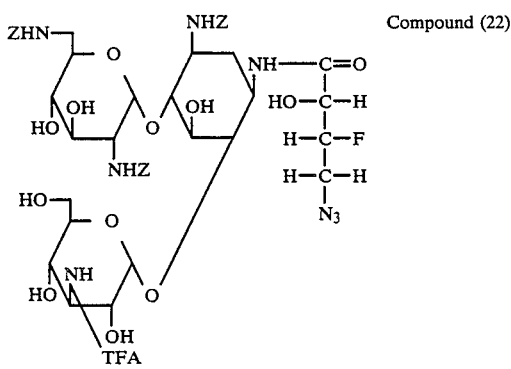

Compound (22)

3,2',6'-Tris(N-benzyloxycarbonyl)-3''-N-trifluoroacetylkanamycin B (150 mg) was dissolved in a mixed solvent (4.5 ml) of tetrahydrofuran and water (2:1). The resultant solution was added with a solution which had been obtained by dissolving in tetrahydrofuran (3 ml) Compound (15) (118 mg) as prepared in Referential Example 1(i) above. The reaction was effected at room temperature for 10 minutes. A 5% aqueous solution of sodium hydrogencarbonate (1.5 ml) was added to the acidic reaction mixture to neutralize same. The reaction mixture was concentrated and the residue was washed successively with water and diethyl ether to obtain the titled Compound (22) as a colorless solid product (156.1 mg). Yield: 91%.

(2) Production of 1-N-{(2R,3R)-4-amino-3-fluoro-2-hydroxybutyryl}kanamycin B (Invention Compound No. 5)

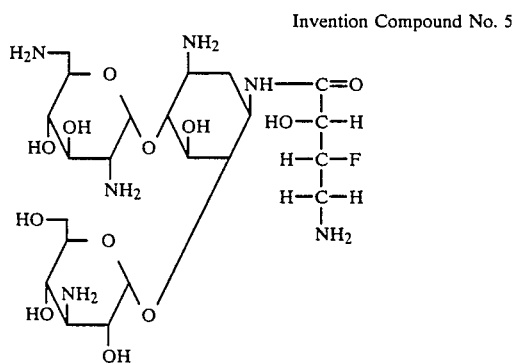

Invention Compound No. 5

Compound (22) (125 mg) obtained in the preceding step (1) was dissolved in a liquid mixture (6 ml) of 3N aqueous ammonia and tetrahydrofuran (1:2). The compound was subjected to a hydrolytic reaction for 24 hours at room temperature to remove the 3''-N-trifluoroacetyl group. The reaction mixture was then concentrated. A solid product obtained was dissolved in a liquid mixture (4.1 ml) of acetic acid, dioxane and water (1:20:20). Into the resultant solution was blown hydrogen gas room temperature in the presence of palladium black as a catalyst, whereby the reaction product was catalytically reduced for 1 hour to convert the azido group into an amino group and also to remove the N-benzyloxycarbonyl group. After filtration of the reaction mixture, the resultant filtrate was concentrated. A solid thus obtained was dissolved in water. The resultant solution was caused to pass through a column of "CM-Sephadex C-25" (trade name) (25 ml). The column was developed gradiently with aqueous ammonia while gradually increasing the concentration of ammonia from 0N to 0.2N. There was collected such eluate fractions (75-95 ml) which were found to contain the intended compound as tested by the ninhydrin reaction. The fractions were concentrated to obtain the titled Invention Compound No. 5 as a colorless solid product (44.3 mg).

$[\alpha]_D^{20}$ +80° (c 1, water)

EXAMPLE 6

(1) Preparation of 1-N-{(2R,3R)-4-azido-3-fluoro-2-hydroxybutyryl}-3,2',6'-tris(N-benzyloxycarbonyl)-3''-N-trifluoroacetyltobramycin {Compound (23)}

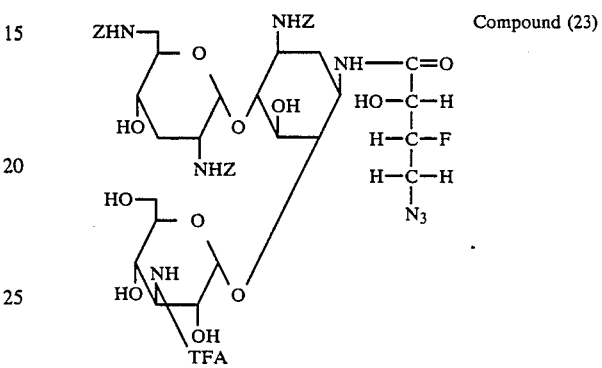

Compound (23)

3,2',6'-Tris(N-benxyloxycarbonyl)-3''-N-trifluoroacetyltobromycin (100 mg) was dissolved in a mixed solvent (4 ml) of tetrahydrofuran and water (3:1). The resultant solution was added with a solution which had been obtained by dissolving in tetrahydrofuran (1.8 ml) Compound (15) (67 mg) as prepared in Referential Example 1(i) above. The reaction was effected at room temperature for 10 minutes. A 5% aqueous solution of sodium hydrogencarbonate (0.4 ml) was added to the acidic reaction mixture to neutralize same, followed by addition of a tetrahydrofuran solution of Compound (15) in the same amount as added above. After the reaction for 10 minutes, a 5% aqueous solution of sodium hydrogencarbonate (1.2 ml) was added further to said reaction mixture. The reaction mixture was then concentrated and the residue was washed successively with water and diethyl ether to obtain the titled Compound (23) as a colorless solid (109.2 mg). Yield: 95%.

(2) Production of 1-N-{(2R,3R)-4-amino-3-fluoro-2-hydroxybutyryl}tobramycin (Invention Compound No. 6)

Compound (23) (103.3 mg) obtained in the preceding step (1) was dissolved in liquid mixture (5 ml) of 5N aqueous ammonia and tetrahydrofuran (1:4). The compound was subjected to a hydrolytic reaction for 24 hours at room temperature to remove the 3''-N-trifluoroacetyl group. The reaction mixture was then concentrated. A solid product so obtained was dissolved in a liquid mixture (4.1 ml) of acetic acid, dioxane and water (1:20:20). Into the solution was blown hydrogen gas at room temperature in the presence of palladium black as a catalyst, whereby the reaction product was catalytically reduced for 2 hours to convert the azido group into an amino group and also to remove the N-benzyloxycarbonyl group. After filtration of the reaction mixture, the resultant filtrate was concentrated. A solid thus obtained was dissolved in water. The resultant solution was caused to pass through a column of "CM-Sephadex C-25" (trade name) (30 ml). The column was developed gradiently with aqueous ammonia while gradually increasing the concentration of ammonia from 0N to 0.2N. Among eluate fractions, those containing the intended compound (80–100 ml) (positive to ninhydrin reaction) were collected and then concentrated to afford the titled Invention Compound No. 6 as a colorless solid (32.3 mg).

$[\alpha]_D^{24}$ +73° (c 0.5, water)

$^1$H-NMR spectrum (in 20% ND$_3$-D$_2$O; internal standard: TMS):

δ 4.25 (1H, dd, H-2'''), 4.87 (1H, dddd, H-3''').

$J_{H-2''',F}=31$, $J_{H-3''',F}=48$, $J_{H-2''',H-3'''}=2 1$ Hz.

EXAMPLE 7

(1) Preparation of 1-N{(2R,3R)-4-azido-3-fluoro-2-hydroxybutyryl}-3,2',6'-tris(n-benzyloxycarbonyl)-3''-N-trifluoroacetyldibekacin {Compound (24)}

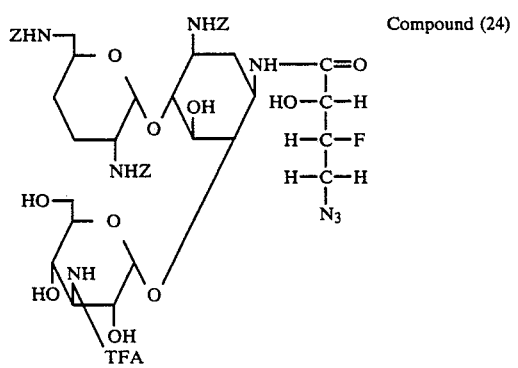

Compound (24)

3,2',6'-Tris(N-benzyloxycarbonyl)-3''-N-trifluoroacetyldibekacin (250 mg) was dissolved in a mixed solvent (7.5 ml) of tetrahydrofuran and water (2:1). The resultant solution was added with a solution which had been obtained by dissolving in tetrahydrofuran (2.5 ml) Compound (15) (102 mg) as prepared in Referential Example 1(i) above, immediately followed by addition of a 5% aqueous solution of sodium hydrogencarbonate (1 ml) to neutralize the acidic reaction mixture. After the reaction was effected at room temperature for 30 minutes, a tetrahydrofuran solution (1.3 ml) of Compound (15) (53 mg) was added further to conduct the reaction. Subsequently, the reaction mixture was neutralized with a 5% aqueous solution of sodium hydrogencarbonate (0.5 ml) The reaction mixture was left over for 0.5 hour at room temperature. The reaction mixture was then concentrated and the residue was washed successively with water and diethyl ether to give the titled Compound (24) as a colorless solid (283 mg). Yield: 98%.

(2) Production of 1-N-{(2R,3R)-4-amino-3-fluoro-2-hydroxybutyryl}dibekacin (Invention Compound No. 7)

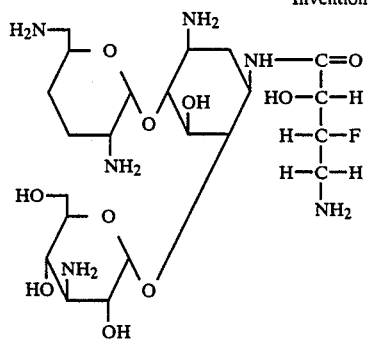

Invention Compound No. 7

Compound (24) (300 mg) obtained in the preceding step (1) was dissolved in a liquid mixture (12 ml) of 4N aqueous ammonia and tetrahydrofuran (1:3). The compound was subjected to a hydrolytic reaction for 24 hours at room temperature to remove the 3''-N-trifluoroacetyl group. The reaction mixture was then concentrated. A solid product so obtained was dissolved in a liquid mixture (12.3 ml) of acetic acid, dioxane and water (1:20:20). Into the resulting solution was blown hydrogen gas at room temperature in the presence of palladium black as a catalyst, whereby the reaction product was catalytically reduced for 1 hour to convert the azido group into an amino group and also to remove the N-benzyloxycarbonyl group. After filtration of the reaction mixture, the resultant filtrate was concentrated. A solid product so obtained was dissolved in water. The resultant solution was caused to pass through a column of "CM-Sephadex C-25" (trade name) (30 ml). The column was developed gradiently with aqueous ammonia while gradually increasing the concentration of ammonia from 0N to 0.15N. Among the eluate fractions, such fractions (360–500 ml) which were positive to the ninhydrin reaction and contained the intended compound were collected together. The fractions were concentrated to obtain the titled Invention Compound No. 7 as a colorless solid (125.3 mg).

$[\alpha]_D^{19}$ =86° (c 1, water)

$^1$H-NMR spectrum (in 20% ND$_3$-D$_2$O; internal standard: TMS):

δ 4.32 (1H, dd, H-2'''), 4.94 (1H, dddd, H-3'''), 5.19 (1H, d, H-1''), 5.21 (1H, d, H-1').

$J_{H-2''',F}=31$, $J_{H-3''',F}=48$ Hz.

EXAMPLE 8

(1) Preparation of 1-N-{(2R,3R)-4-azido-3-fluoro-2-hydroxybutyryl}-3,2',6'-tris(N-benzyloxycarbonyl)-5-deoxy-5-fluoro-3''-N-trifluoroacetylkanamycin B {Compound (26)}

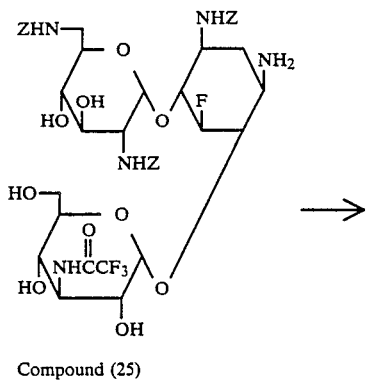

Compound (25)

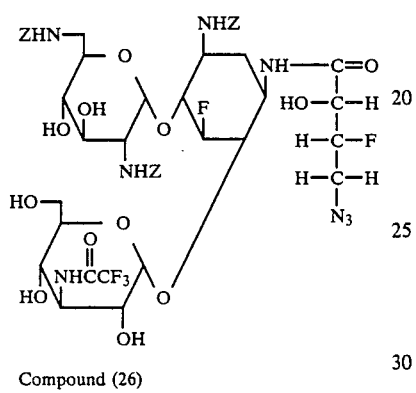

Compound (26)

Compound (25) represented by the above formula, namely, 3,2',6'-tris(N-benzyloxycarbonyl)-5-deoxy-5-fluoro-3"-N-trifluoroacetylkanamycin B (whose preparation process is described in the specification of Japanese patent application No. 181850/86 or U.S. patent application Ser. No. 078,996 assigned commonly to the present assignee) (150 mg) was dissolved in a mixed solvent (6 ml) of tetrahydrofuran and water (3:1). The resultant solution was added with a solution which had been obtained by dissolving in tetrahydrofuran (2.7 ml) Compound (15) (101 mg) as prepared obtained in Referential Example 1(i) above. After the reaction was effected for 10 minutes at room temperature, a 5% aqueous solution of sodium hydrogencarbonate (0.6 ml) was added to the reaction mixture to neutralize same. A tetrahydrofuran solution of Compound (15) in the same amount as added above was again added to the reaction mixture. After the reaction for 10 minutes, a 5% aqueous solution of sodium hydrogencarbonate (1.8 ml) was added similarly to the reaction mixture. The reaction mixture was then concentrated and the residue was washed successively with water and diethyl ether to obtain the titled Compound (26) (160 mg).

(2) Production of 1-N-{(2R,3R)-4-amino-3-fluoro-2-hydroxybutyryl}-5-deoxy-5-fluorokanamycin B (Invention Compound No. 8)

Compound (26) (151 mg) obtained in the preceding step (1) was dissolved in a liquid mixture (7.3 ml) of 5N aqueous ammonia and tetrahydrofuran (1:4). The compound was subjected to a hydrolytic reaction for 24 hours at room temperature to remove the 3"-N-trifluoroacetyl group. The reaction mixture was then concentrated. A solid product so obtained was dissolved in a liquid mixture (5.9 ml) of acetic acid, dioxane and water (1:20:20). Into the solution was blown hydrogen gas at room temperature in the presence of palladium black as a catalyst, whereby the reaction product was catalytically reduced for 2 hours to convert the azido group into an amino group and also to remove the N-benzyloxycarbonyl group. After filtration of the reaction mixture, the resultant filtrate was concentrated. A solid product so obtained was dissolved in water. The resultant solution was caused to pass through a column of "CM-Sephadex C-25" (trade name). The column was developed gradiently with aqueous ammonia while gradually increasing the concentration of ammonia from 0N to 0.2N. Fractions containing the intended compound were collected and then concentrated to afford the titled Invention Compound No. 8 (48.2 mg).

$[\alpha]_D^{25}$ +81° (c 1, water)

EXAMPLE 9

(1) Preparation of 1-N-{(2R,3R)-4-azido-3-fluoro-2-hydroxybutyryl}-3,2',6'-(N-benzyloxycarbonyl)-5-deoxy-5-fluoro-3"-N-trifluoroacetyltobramycin {Compound (28)}

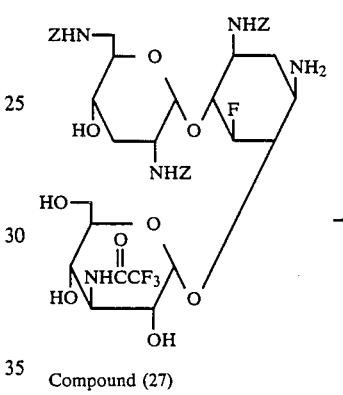

Compound (27)

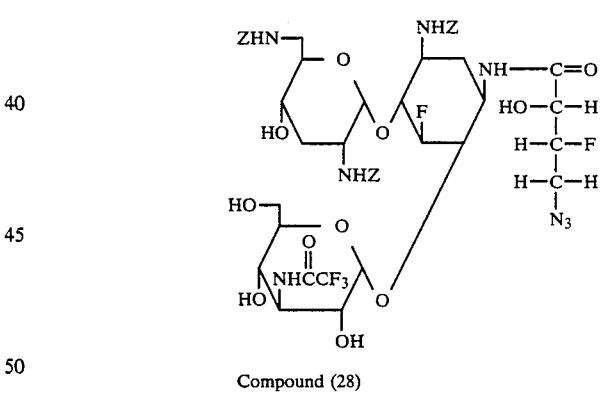

Compound (28)

Compound (27) represented by the above formula, namely 3,2',6'-tris(N-benzyloxycarbonyl)-5-deoxy-5-fluoro-3"-N-trifluoroacetyltobramycin (whose preparation process is described in the specification of Japanese patent application No. 181850/86 or U.S. patent application Ser. No. 078,996) (132 mg) was dissolved in a mixed solvent (5.3 ml) of tetrahydrofuran and water (3:1). The resultant solution was added with a solution which had been obtained by dissolving in tetrahydrofuran (2.4 ml) Compound (15) (89 mg) as prepared in Referential Example 1(i) above. After the reaction was effected for 10 minutes at room temperature, a 5% aqueous solution of sodium hydrogencarbonate (0.53 ml) was added to the reaction mixture to neutralize same. A tetrahydrofuran solution of Compound (15) in the same amount as added above was again added to the reaction mixture. After the reaction for 10 minutes, a 5% aqueous solution of sodium hydrogencarbonate (1.6 ml) was added similarly to the reaction mixture. The reaction mixture was then concentrated and the residue was washed successively with water and diethyl ether to obtain the titled Compound (28) (144.5 mg).

(2) Production of 1-N-{(2R,3R)-4-amino-3-fluoro-2-hydroxybutyryl}-5-deoxy-5-fluorotobramycin (Invention Compound No. 9)

Compound (28) (110 mg) obtained in the preceding step (1) was dissolved in a liquid mixture (5.3 ml) of 5N aqueous ammonia and tetrahydrofuran (1:4). The compound was subjected to a hydrolytic reaction for 24 hours at room temperature to remove the 3''-N-trifluoroacetyl group. The reaction mixture was then concentrated. A solid product so obtained was dissolved in a liquid mixture (4.4 ml) of acetic acid, dioxane and water (1:20:20). Into the resultant solution was blown hydrogen gas at room temperature in the presence of palladium black as a catalyst, whereby the reaction product was catalytically reduced for 2 hours to convert the azido group into an amino group and also to remove the N-benzyloxycarbonyl group. After filtration of the reaction mixture, the resultant filtrate was concentrated. A solid product so obtained was dissolved in water. The resultant solution was caused to pass through a column of "CM-Sephadex C-25" (trade name). The column was developed gradiently with aqueous ammonia while gradually increasing the concentration of ammonia from 0N to 0.2N. Fractions containing the intended compound were collected and then concentrated to afford the titled Invention Compound No. 9 (35.2 mg).

$[\alpha]_D^{20}$ +83° (c 1, water)

EXAMPLE 10

(1) Preparation of 1-N-{(2R,3R)-4-azido-3-fluoro-2-hydroxybutyryl}-3,2',6'-tris(N-benzyloxycarbonyl)-5-deoxy-5-fluoro-3''-N-trifluoroacetyldibekacin {Compound (30)}

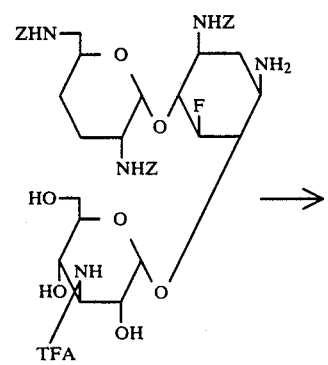

Compound (29)

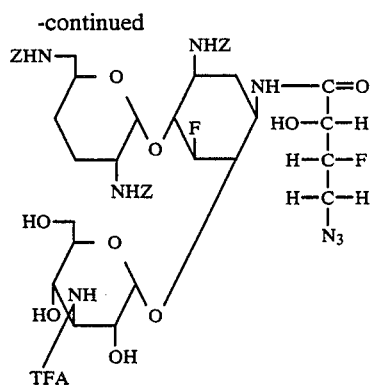

Compound (30)

Compound (29) represented by the above formula, namely, 3,2',6'-tris(N-benzyloxycarbonyl)-5-deoxy-5-fluoro-3''-N-trifluoroacetylbidekacin (which is described in the specification of Japanese patent application No. 181850/86 or U.S. patent application Ser. No. 078.996) (112 mg) was dissolved in a 3:1 mixed solvent (4.5 ml) of tetrahydrofuran and water. The resultant solution was added with a solution which had been obtained by dissolving in tetrahydrofuran (2.8 ml) Compound (15) (92 mg: threefold molar proportions as prepared in Referential Example 1(i) above. After the reaction was effected for 15 minutes, a 5% aqueous solution of sodium hydrogen carbonate (0.55 ml) was added to the reaction mixture. The reaction mixture was then concentrated under reduced pressure and the residue was washed successively with water (10 ml×4) and diethyl ether (10 ml×3) to give the titled Compound (30) as a pale yellow solid (119 mg). Yield: 92%.

(2) Synthesis of 1-N-{(2R,3R)-4-amino-3-fluoro-2-hydroxybutyryl}-5-deoxy-5-fluorodibekacin (Invention Compound No. 10)

Compound (30) (97 mg) obtained in the preceding step (1) was dissolved in a liquid mixture (5.3 ml) of 5 N aqueous ammonia and tetrahydrofuran (1:4). The compound was subjected to a hydrolytic reaction at room temperature. After the reaction for 20 hours, the reaction mixture was concentrated under reduced pressure to obtain the de-trifluoroacetylated derivative (96 mg) as a solid. The de-trifluoroacetylated derivative (96 mg) was dissolved in a liquid mixture (6.7 ml) of dioxane, acetic acid and water (4:1:1). Ten droplets of an aqueous suspension of palladium black were added to the resultant solution, followed by blowing of hydrogen gas thereinto under normal pressure so that the reaction product was catalytically reduced for 2 hours. Thereafter, the catalyst was filtered off and palladium was washed with water. The filtrate and washing were combined together, followed by concentration under reduced pressure. A solid product so obtained was dissolved in water. The resultant solution was charged into a column of "CM-Sephadex C-25" (trade name) (30 ml), and the column was washed with water and was then eluted gradiently with aqueous ammonia while gradually increasing the concentration of ammonia from 0.05N to 0.2N continuously. Relevant fractions containing the desired product were combined and then concentrated to dryness, thereby affording the titled Compound No. 10 of this invention as a colorless solid (33.5 mg). Yield: 58% (as monocarbonate and monohydrate)

$[\alpha]_D^{20}$ +86° (c 1, water)

Incidentally, Compound (20) as used in Example 4, namely, 3,6'-bis(N-benzyloxycarbonyl)-5-deoxy-5-fluoro-3''-N-trifluoroacetylkanamycin A is a novel compound. It was prepared by protecting 5-deoxy-5-fluorokanamycin A, which is also a novel compound synthesized newly by the present inventors, according to the amino-group protecting technique as described in Examples 1 and 33 of U.S. Pat. No. 4,297,485. A process for the synthesis of 5-deoxy-5-fluorokanamycin A will next be described in Referential Example 2. In the respective formulae as shown in Referential Example 2, Ac, Z and Ms will denote an acetyl group, a benzyloxycarbonyl group and a mesyl group (—SO$_2$CH$_3$), respectively.

REFERENTIAL EXAMPLE 2

(1) Synthesis of 2',3',4',2'',4'',6''-hexa-O-acetyl-1,3,6',3''-tetrakis(N-benzyloxycarbonyl) kanamycin A (Compound a)

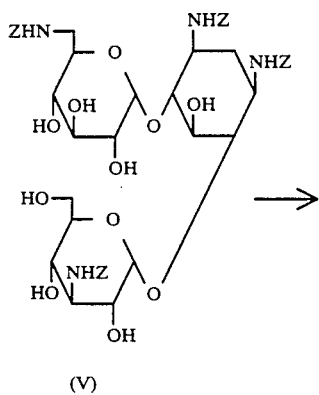

(V)

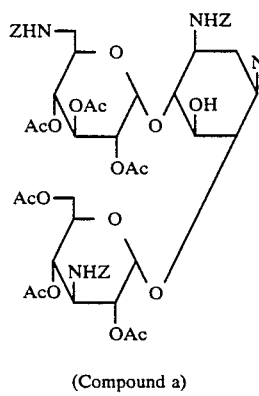

(Compound a)

1,3,6-',3'''-Tetrakis(N-benzyloxycarbonyl) kanamycin A represented by the above formula (V) (6 g) was dissolved in dry pyridine (120 ml), followed by addition of dry acetic acid (13.31 ml). The reaction was effected overnight at room temperature (for the acetylation). After adding water (12.7 ml) to the reaction mixture, the resultant mixture was concentrated under reduced pressure. The residue was extracted with chloroform, and the resulting solution in chloroform was washed successively with a 10% aqueous solution of potassium hydrogen sulfate, a saturated aqueous solution of sodium hydrogen carbonate and water and was then dried over anhydrous sodium sulfate. Then dried solution was concentrated to dryness under reduced pressure to yield the titled Compound (a) (8.13 g).

$[\alpha]_D^{20}$ +73° (c 1.08, chloroform)

(2) Synthesis of 2',3',4',2'',4'',6''-hexa-O-acetyl-1,3,6',3''-tetrakis(N-benzyloxycarbonyl)-5-O-mexylkanamycin A (Compound b)

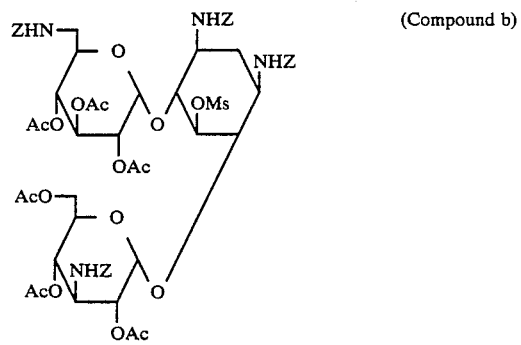

(Compound b)

Compound (a) (7.4 g) obtained in the preceding step was dissolved in dry dichloromethane (148 ml), followed by addition of 4-dimethylaminopyridine (21.3 g). While stirring the resultant mixture under ice cooling, mesyl chloride (as the mesylating agent) (6.75 ml) was added thereto. The reaction was effected at room temperature for 2 hours (for the mesylation of the 5-hydroxyl group). Thereafter, water (7.85 ml) was added to the reaction mixture and the resultant mixture was stirred throughly. The mixture was then diluted with chloroform (500 ml). After washing the mixture successively with water, a 10% aqueous solution of potassium hydrogen sulfate, a saturated aqueous solution of sodium hydrogen carbonate and water, the mixture was dried over anhydrous sodium sulfate. The resultant dried solution was concentrated to dryness under reduced pressure, to afford the titled Compound (b) (8.3 g).

$[\alpha]_D^{20}$ +69° (c 1.08, chloroform)

(3) Synthesis of 5,2',3',4',2'',4'',6''-hepta-O-acetyl-1,3,6',4'''-tetrakis(N-benzyloxycarbonyl)-5-epikanamycin A (Compound c)

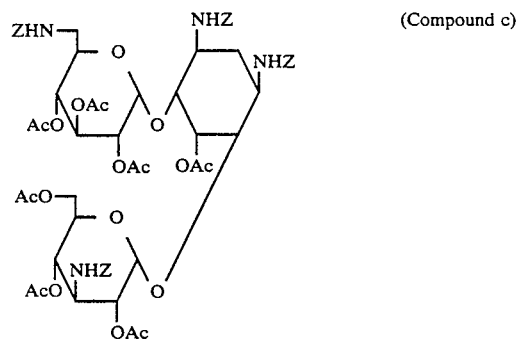

(Compound c)

Compound (b) (8.1 g) obtained in the preceding step was dissolved in dry dimethylformamide (405 ml), followed by addition of anhydrous sodium acetate (4.91 g). While stirring the resultant mixture vigorously at 100° C., the reaction was effected for 20 hours (for the acetylation and epimerization at the 5-position). The reaction mixture was concentrated under reduced pressure and the residue was extracted with chloroform. After washing the resultant extract in chloroform with water, the solution (the extract) was dried over anhydrous sodium sulfate. The solution was concentrated to dryness under reduced pressure to obtain the titled Compound (c) (8.1 g).

$[\alpha]_D^{20}$ +56° (c 0.98, chloroform)

(4) Synthesis of 1,3,6',3''-tetrakis(N-benzyloxycarbonyl)-5-epikanamycin A (Compound d)

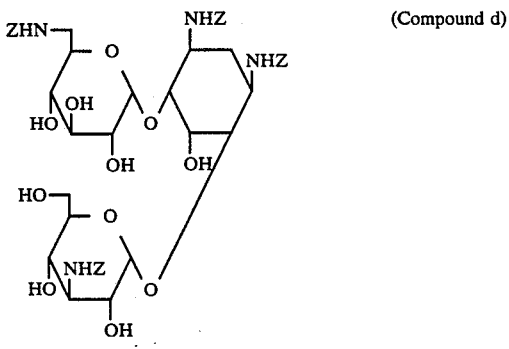

Compound (c) (5 g) obtained in the preceding step was dissolved in a mixed solvent of methanol (200 ml) and water (20 ), followed by addition of sodium carbonate (5.64 g). The mixture obtained was stirred vigorously at room temperature for 2 hours, to effect the hydrolysis (for the deacetylation). After neutralizing the reaction mixture with dilute hydrochloric acid, the reaction mixture was concentrated under reduced pressure. The residue was washed with a large amount of water and then dried to obtain the titled Compound (d) (3.1 g).

$[\alpha]_D^{20}$ +74° (c 0.88, pyridine)

(5) Synthesis of 2',3',4',2'',4'',6'',-hexa-O-acetyl-1,3,6',3''-tetrakis(N-benzyloxycarbonyl)-5-epikanamycin A (Compound e)

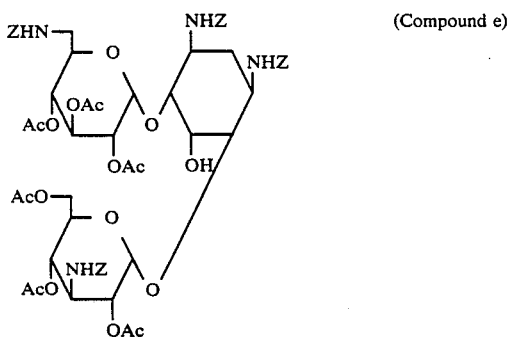

Compound (d) (4.02 g) obtained in the preceding step was dissolved in dry pyridine (80.5 ml), followed by addition of acetic anhydride (11.1 ml). The reaction was effected overnight at room temperature (for the acetylation). After adding water (10.6 ml) to the reaction mixture, the resultant mixture was concentrated under reduced pressure. The residue was extracted with chloroform, and the resulting extract in chloroform was washed successively with a 10% aqueous solution of potassium hydrogen sulfate, a saturated aqueous solution of sodium hydrogen carbonate and water and was then dried over anhydrous sodium sulfate. The dried solution was concentrated to dryness under reduced pressure to obtain the titled Compound (e) (5.24 g).

$[\alpha]_D^{29}$ +77° (c 0.84, chloroform)

(6) Synthesis of 2',3',4',2'',4'',6'',-hexa-O-acetyl-1,3,6',3''-tetrakis(N-benzyloxycarbonyl)-5-deoxy-5-fluorokanamycin A (Compound f)

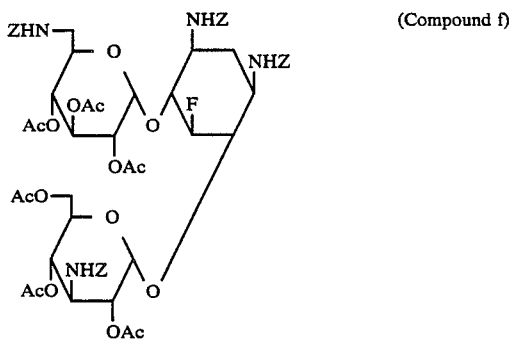

Diethylaminosulfur trifluoride (as a fluorinating agent) (2.25 ml) was diluted with dry dichloromethane (78.1 ml), to which was added at 0° C. such a solution which had been obtained by dissolving the Compound (e) (4.7 g) as obtained in the preceding step, in a mixed solvent of dry dichloromethane (156 ml) and dry pyridine (4.5 ml). The reaction was conducted for 1 hour at room temperature {for the fluorination and concommitant steric inversion of 5-hydroxyl group; see "Chemical Abstracts" 90,104, 301 (1979)}. The reaction mixture was thereafter poured into a saturated aqueous solution of sodium hydrogen carbonate (234 ml) which had been ice-cooled. The resultant mixture was extracted with chloroform (250 ml). The resulting extract in chloroform was washed successively with a saturated aqueous solution of sodium hydrogen carbonate and water, and was then dried over anhydrous sodium sulfate. The solution was concentrated to dryness under reduced pressure, to yield the titled Compound (f) (4.8 g).

$[\alpha]_D^{20}$ +90° (c 1.05, chloroform)

Elemental analysis:
Calculated for $C_{67}H_{71}FN_4O_{24}$: C, 58.39; H, 5.61; N, 4.39; F,1.49, Found: C, 58.27; H, 5.68; N, 4.50; F, 1.48.

$^{19}$F-NMR spectrum (in pyridine-$d_5$; internal standard: tridhlorofluoromethane): δ −188.88 (dt).

(7) Synthesis of 13,6,',3''-tetrakis(N-benzyloxycarbonyl)-5-deoxy-5-fluorokanamycin A (Compound g)

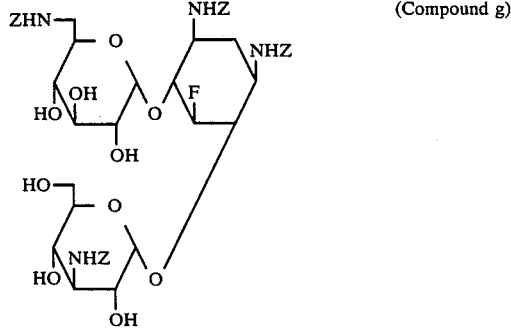

Compound (f) (1.4 g) obtained in the preceding step was dissolved in a mixed solvent of methanol (56 ml) and water (5.6 ml), followed by addition of sodium carbonate (1.63 g). The resulting mixture was stirred vigorously at room temperature for 2 hours, to effect the hydrolysis (for the de-acetylation). After adding dilute hydrochloric acid to the reaction mixture to neutralize same, the resultant mixture was concentrated to dryness under reduced pressure. The residue was washed with a large volume of water and then dried to obtain the titled Compound (g) (1.05 g).

$[\alpha]_D^{20}$ +85° (c 1.0, pyridine)

(8) Synthesis of 5-deoxy-5-fluorokanamycin A (Compound h)

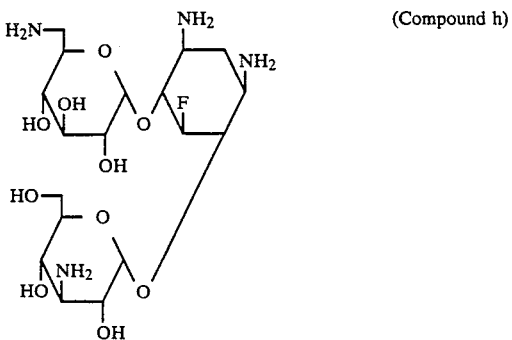
(Compound h)

Compound (g) (820 mg) obtained in the preceding step was dissolved in a mixture (49 ml) of dioxane, water and acetic acid (4:1:1), and the resulting solution was subjected to catalytic reduction in the presence of palladium black as a catalyst at room temperature for 1 hour so as to remove the N-benzyloxycarbonyl group from Compound (g). After filtration of the reaction mixture, the filtrate was concentrated and a solid product so obtained was dissolved in water. The solution was charged onto a column of "CM-Sephadex C-25" (trade name). The column was thereafter developed gradiently with aqueous ammonia while gradually increasing the concentration of ammonia from 0N to 0.15N. Fractions containing the desired compound were collected and then concentrated to give the titled Compound (h) as a colorless solid (312 mg).

$[\alpha]_D^{23}$ +145° (c 1.0, water)

Elemental analysis:
Calculated for $C_{18}H_{35}FN_4O_{10}$: C 44.44; H 7.25; N 11.52; F 3.91% Found: C 44.13; H 7.41; N 11.28; F 3.72%

$^1$H-NMR spectrum (in DCl-D$_2$O; internal standard: TMS):
δ 2.09 (1H, q, H-2ax), 2.67 (1H, dt, H-2eq), 4.26 (1H, broad q, H-4 or H-6), 4.37 (1H, broad q, H-6 or H-4), 5.07 (1H, dt, H-5), 5.25 (1H, d, H-1''), 5.55 (1H, d, H-1').

$^{19}$F-NMR spectrum (in DCl-D$_2$O; external standard: trichlorofluoromethane): δ -192.70 (dt).

$^{13}$C-NMR spectrum (in DCl-D$_2$O; internal standard: dioxane):
δ 92.5 (d, C-5).
$J_{C-5,F}$=183.7 Hz.

Upon the production of the new compounds of the formula (I) according to this invention, 5-deoxy-5-fluorokanamycin B, 5,3'-dideoxy-5-fluorokanamycin B (namely, 5-deoxy-5-fluorotobramycin), and 5,3',4'-trideoxy-5-fluorokanamycin B(namely, 5-deoxy-5-fluorodibekacin) which are described in the specifications of Japanese patent application No. 181850/86; U.S. patent application Ser. No. 078,996 and European patent application No. 87306904.1 (as scheduled to be published at 9 March 1988 under European patent application Ser. No. 0259014), are employed as the starting compound in the process of the third aspect of this invention. These new 5-deoxy-5-fluorokanamycin B derivatives set out above may be represented by a general formula

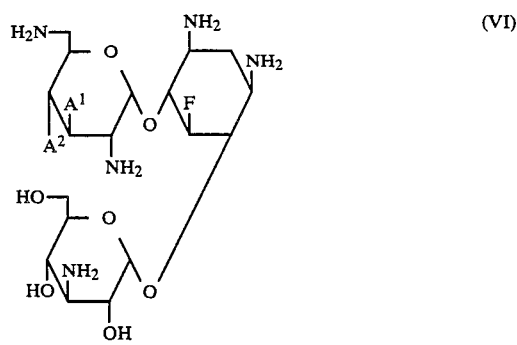
(VI)

wherein $A^1$ and $A^2$ are each a hydroxyl group for 5-deoxy-5-fluorokanamycin B; $A^1$ is a hydrogen atom and $A^2$ is a hydroxyl group for 5,3'-dideoxy-5-fluorokanamycin B; and $A^1$ and $A^2$ are each a hydrogen atom for 5,3',4'-trideoxy-5-fluorokanamycin B. Now, descriptions are made of a process for the preparation of the 5-deoxy-5-fluorokanamycin B derivatives of the general formula (VI). In short, the compounds of the formula (VI) may be prepared according to a process for the preparation of 5-deoxy-5-fluorokanamycin B or a derivative thereof represented by the formula (VI).

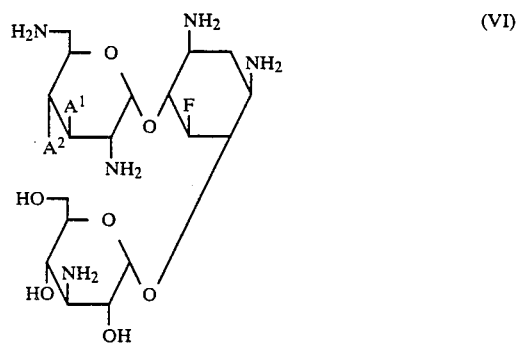
(VI)

wherein $A^1$ and $A^2$ are independently a hydroxyl group or a hydrogen atom, as defined just above, which comprises (i) reacting an N,O-protected 5-epi-kanamycin B derivative represented by the general formula

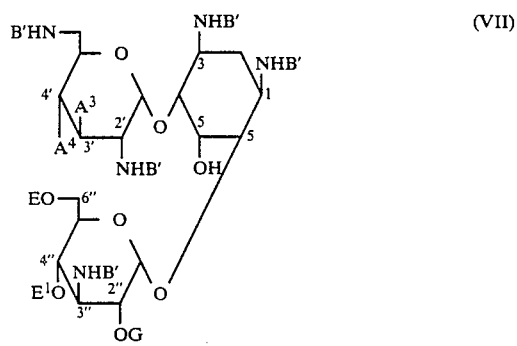
(VII)

wherein $A^3$ and $A^4$ are independently a protected hydroxyl group —OG or a hydrogen atom, where G denotes an acyl group as the hydroxyl-protecting group, B' is an amino-protecting group, and E and $E^1$ are each an acyl group of the same nature as the aforesaid group G and are the hydroxyl-protecting group, or E and $E^1$ as taken together form a di-valent hydroxyl-protecting group; and the group G present at the 2"-hydroxyl group is an acyl group of the same nature as the aforesaid group G and is the hydroxyl-protecting group, with a dialkylamniosulfur trifluoride of the formula

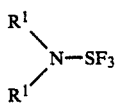 (VIII)

wherein $R^1$ is an alkyl group of 1 to 4 carbon atoms, or with a bis(dialkylamino)-sulfur difluoride of the formula

 (VIII')

wherein $R^1$ is as defined above, or with a fluorination agent equivalent to the compound of formula (VIII) or (VIII') in a non-polar organic solvent, to effect the steric inversion of the eip-hydroxyl group at the 5-position of the compound of formula (VII) and also the replacement of the 5-hydroxyl group by a fluoro substitutent, thereby producing an N,O-protected 5-deoxy-5-fluorokanamycin B derivative represented by the formula

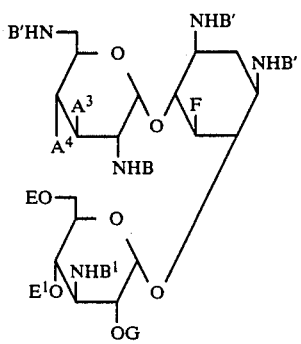 (IX)

wherein $A^3$, $A^4$, B', E, $E^1$ and G are as defined above, and then (ii) removing the remaining amino-protecting group (B') and the remaining hydroxyl-protecting groups (E, $E^1$ and G) from the compound of formula (IX) in a known manner.

Firstly, the preparation of the N,O-protected 5-epi-kanamycin B derivatives of formula (VII) mentioned just will be described hereinafter.

Thus, in the course of our studying a process for the synthetic production of 5-deoxy-5-fluorokanamycin B, and as an outcome of our study, we have found that, first of all, such a special type of an N,O-protected derivative of kanamycin B whose all the amino groups and all the hydroxyl groups except the 5-hydroxyl group have been blocked with suitable protective groups is needed as an intermediate raw material to be substituted by the fluoro group at the 5-position thereof. Accordingly, we have continued our study with object to provide a method for preparing such special type of the N,O-protected kanamycin B derivative, and as a result, we have succeeded in synthesizing a 3',4',2",4",6"-penta-O-protected-1,3,2',6',3"-penta-N-protected(sulfonylated)-kanamycin B having the free 5-hydroxyl group by such a method which comprises selecting an amino-protecting group of the sulfonyl type from amongst many and various kinds of known amino-protecting groups, introducing the amino-protecting group of the sulfonyl type into all the amino groups of kanamycin B for the protection of the amino groups and then reacting the resulting N-protected (sulfonylated)-kanamycin B derivative with an acyl chloride, preferably acetyl chloride in anhydrous pyridine at a low temperature of 0° C. or less to acylate selectively all the hydroxyl groups other than the 5-hydroxyl group of the kanamycin B molecule; or alternatively by such a method which comprises blocking both the 4"- and 6"-hydroxyl groups of kanamycin B simultaneously with a di-valent hydroxyl-protecting group such as an alkylidene group and then reacting the resulting 4",6"-di-O-protected kanamycin B derivative with an acyl halogenide, acyl anhydride or N-acyl-imidazole under selected reaction conditions for the protection of all the hydroxyl groups other than the 5-hydroxyl group, so that the 5-hydroxyl group is not acylated while the 3'-, 4'- and 2"-hydroxyl groups are selectively acylated.

Furthermore, we have recognized that the replacement by the fluoro group of the 5-hydroxyl group of the above-mentioned special type of the N,O-protected kanamycin B derivative may successfully be achieved by reacting with diethylaminosulfur trifluoride (abfreviated as DAST) or the other dialkylaminosulfur trifluoride or a bis-(dialkylamino)-sulfur difluoride which can give a good efficiency of the fluorination under mild reaction conditions (see "J. Org. Chem." 40, No. 5, pages 574–578 (1975)). While, we have noticed also that when the dialkylaminosulfur trifluoride or bis-(dialkylamino)-sulfur difluoride is reacted with the above-mentioned 3',4',2",4",6"-penta-O-protected-1,3,2',6'3"-penta-N-protected (sulfonylated)-kanamycin B, disadvantageously, the steric arrangement of the 5-substituent can inevitably be inverted from the original disposition of the 5-hydroxyl group, simultaneously to the replacement thereof by the fluoro substituent, thereby giving a 5-deoxy-5-fluoro-5-epi-kanamycin B derivative. As a result of our continued study, we have expected that our object might be achieved if we would prepare at first a suitable N,O-protected 5-epi-kanamycin B derivative by effecting exclusively the steric inversion of the 5-hydroxyl group of a suitable N,O-protected kanamycin B before this N,O-protected kanamycin B is reacted with the fluorination agent such as DAST to replace its 5-hydroxyl group by the fluoro group; and if we would react the above suitable N,O-protected 5-epi-kanamycin B derivative with the fluorination agent such as DAST to effect the second inversion of the 5-epi-substituent and the simultaneous substitution by the fluoro group at the 5-position, whereby the intended suitable, N,O-protected 5-deoxy-5-fluorokanamycin B derivative which is not in the 5-epimer form would successfully be produced in an ingenious way. We have thus continued our research to discover that the steric inversion of the 5-hydroxyl group of the above-mentioned 3',4',2",4",6"-penta-O-protected-1,3,2',6',3"-penta-N-protected(sulfonylated)-kanamycin B can be achieved at good efficiency by reacting the latter N,O-protected kanamycin B derivative with triphenylphosphine [$P(C_6H_5)_3$], diethyl azodicarboxylate ($C_2H_5-O_2C-N=N-CO_2-C_2H_5$) and an organic acid such as benzoic acid together according to Mitsunobu's reaction (see O. Mitsunobu & Y. Yamada "Bull. Chem. Soc. Jpn." 40, 2380 (1967)). Thus, we have prepared from the above-mentioned N,O-protected kanamycin B derivative a 5-O-benzoyl-5-eip-3',4',2'',4'',6''-penta-O-protected-1,3,2',6',3''-penta-N-protected(sulfonylated)-kanamycin B according to the Mitsunobu's reaction, and then treated the latter compound with a methanolic solution of sodium methoxide to remove the benzoyl group from the 5-epi-hydroxyl group and remove the acyl groups from the 3'-, 4'-, 2''-, 4''- and 6''-hydroxyl groups thereof or alternatively remove the acyl groups from the 3'-, 4'- and 2''-hydroxyl group thereof (in case where the 4''- and 6''-hydroxyl groups have been protected by a di-valent hydroxyl-protecting group), and thereby to afford a corresponding 1,3,2',6',3''-penta-N-protected-5-epi-kanamycin B or alternatively a corresponding 4,6''-di-O-protected-1,3,2',6',3''-penta-N-protected-5-epi-kanamycin B. We have subsequently treated the latter protected 5-epi-kanamycin B derivative so obtained by reacting with an N-acyl-imidazole or other acylating agent in the same manner as described above, to acylate selectively all the hydroxyl groups other than the 5-hydroxyl group of the 5-epi-kanamycin B compound, without involving the acylation of the 5-hydroxyl group. In this way, we have succeeded in preparing a 3',4',2'',4'',6''-penta-O-protected-1,3,2',6',3''-penta-N-protected(sulfonylated)-5-epi-kanamycin B. When the latter N,O-protected 5-epi-kanamycin B derivative is reacted with DAST or another dialkylaminosulfur trifluoride or a bis-(dialkylamino)-sulfur di-fluoride or an equivalent fluorination agent thereof to produce a 3',4',2'',4'',6''-penta-O-protected-1,3,2',6'-3''-penta-N-protected(sulfonylated)-5-deoxy-5-fluorokanamycin B, from which are then removed all the amino-protecting groups and the hydroxyl-protecting groups according to the conventinal deprotection techniques, there is successfully produced the desired 5-deoxy-5-fluorokanamycin B with starting from kanamycin B.

Moreover, we have found that the amino-protecting groups which are present in the above-mentioned 3',4',2'',4'',6''-penta-O-protected-1,3,2',6',3''-penta-N-protected(sulfonylated)-kanamycin B, whose the 5-hydroxyl group is to be sterically inverted according to the Mitsunobu's reaction as made in the above process of synthetizing 5-deoxy-5-fluorokanamycin B from kanamycin B, shall be ones of an alkylsulfonyl group such as mesyl; an aralkylsulfonyl group such as benzysulfonyl; and an arylsulfonyl group such as tosyl, as otherwise the Mitsunobu's reaction could not proceed smoothly, and also that tosyl group is then a most preferred amino-protecting group. On the other hand, it has been found that the reaction for the steric inversion of the 5-epi-hydroxyl group and the replacement of the hydroxyl group by the fluoro group through the treatment with the fluorination agent such as DAST can proceed to a sufficient extent, even when the amino-protecting groups present in the N,O-protected 5-epi-kanamycin B derivative to be treated with said fluorination agent do not belong to the aforesaid amino-protecting group of the sulfonyl type. Therefore, we have found that 5-deoxy-5-fluorokanamycin B can be synthetized also according to such a process which comprises treating the above 3',4',2'',4'',6''-penta-O-protected-1,3,2',6',3''-penta-N-protected(sulfonylated)-5-epi-kanamycin B with an alkali metal in liquefied ammonia, thus removing all the amino-protecting groups of the sulfonyl type therefrom to produce a 3',4',2'',6''-penta-O-protected and N-unprotected-5-epi-kanamycin B, then protecting all the amino groups of the latter O-protected 5-epi-kanamycin B derivative by introducing thereinto any optional, known amino-protecting groups, inclusive of an acyl group, for example, an alkanoyl groups such as acetyl; an aroyl group such as benzoyl; an alkoxycarbonyl group such as ethoxycarbonyl and tert.butoxycarbonyl; an aralkyloxycarbonyl group such as benzyloxycarbonyl; an aryloxycarbonyl group such as phenoxycarbonyl; and an amino-protecting group of the Schiff's base type such as benzylidene group and p-nitrobenzylidene group, to yield as 3',4',2'',4'',6''-penta-O-protected-1,3,2',6',3''-penta-N-protected (i.e., as protected by the N-protecting method other than sulfonylation)-5-epi-kanamycin B, and then reacting the 5-hydroxyl group of the latter compound with the fluorination agent such as DAST to produce a corresponding N,O-protected-5-deoxy-5-fluorokanamycin B, followed by removing all the protective groups therefrom. Accordingly, for instance, 3',4',2'',4'',6''-penta-O-benzoyl-1,3,2',6',3''-pentakis(N-ethoxycarbonyl)-5-epi-kanamycin B which was employed as an intermediate product in the method of Suami et al for the synthesis of 5-epi-kanamycin B (see "Bulletin of the Chemical Society of Japan" Vol. 52. No. 3, 955-956 (1979)) may also be converted into a corresponding N,O-protected 5-deoxy-5-fluorokanamycin B of formula (IX) by reacting with the fluorination agent such as DAST.

Moreover, we have found that the above-described processes for the protection of the amino groups and all the hydroxyl groups except the 5-hydroxyl group of kanamycin B; and the Mitsunobu's reaction for effecting the inversion of the 5-hydroxyl group which is applied to kanamycin B; as well as the process for the fluorination and inversion of the epi-disposited 5-hydroxyl group which is effected by reacting the epi-5-hydroxyl group with a dialkylaminosulfur trifluoride such as DAST or a bis(dialkylamino)-sulfur difluoride or an equivalent fluorination agent thereof are effectively applicable to 3'-deoxykanamycin B, 4'-deoxykanamycin B and 3',4'-dideoxykanamycin B which are all the deoxy-derivatives of kanamycin B, and thus we have succeeded in synthetizing 5,3'-dideoxy-5-fluorokanamycin B from 3'-deoxykanamycin B (namely, tobramycin); 5,4'-dideoxy-5-fluorokanamycin B from 4'-deoxykanamycin B (see the "Bull. Chem. Soc. Jpn." 50, page 2362 (1977)); and 5,3',4'-trideoxy-5-fluorokanamycin B from 3',4'-dideoxykanamycin B (namely, dibekacin).

In this way, we have succeeded in preparing the N,O-protected 5-epi-kanamycin B derivative of the general formula (VII) given hereinbefore.

In the N,O-protected 5-epi-kanamycin B derivative of the general formula (VII) so prepared, the amino-protecting group (B') for each of the five amino groups at 1-, 3-, 2'-, 6'-and 3''-positions of the compounds of formula (VII) may be any of the known amino-protecting groups which are insusceptible to the reaction intended, and it may be, for example, an acyl group, including an alkanoyl group such as acetyl and trifluoroacetyl; and an aroyl group such as benzoyl; an alkoxycarbonyl group such as methoxycarbonyl, ethoxycarbonyl and butoxycarbonyl; an aralkyloxycarbonyl group such as benzyloxycarbonyl and phenetyloxycarbonyl; an arloxycarbonyl group such as phenoxycarbonyl and methoxyphenoxycarbonyl; and a sulfonyl type group, including an alkylsulfonyl group, an aralkylsulfonyl group such as benzylsulfonyl and an arylsulfonyl group such as tosyl.

In cases where the compound of formula (VII) has the hydroxyl group(s) at the 3'- and/or 4'-position thereof, it is necessary that the hydroxyl groups at the 3'-and/or 4'-position and the 2"-position should be protected by a known hydroxyl-protecting group (G) which may be selected from an acyl group, preferably an alkanoyl or an aroyl group. Similarly, the 4"- and 6"-hydroxyl groups are necessary to have been protected by known hydroxyl-protecting groups (E, E$^1$) which may be selected from an acyl group, preferably an alkanoyl or an aroyl group. The acyl group for the protection of an hydroxyl group may be an alkanoyl group, typically an alkanoyl group of 2-5 carbon atoms such as acetyl, propionyl and butyryl, or an aroyl group, typically phenylcarbonyl which may have alkyl substituent(s) on the phenyl ring, preferably benzoyl. Alternatively, the 4"-hydroxyl-protecting group (E$^1$) and 6"-hydroxyl-protecting group (E) as taken together may form a single known di-valent hydroxyl-protecting group, for example, an alkylidene group of 2-8 carbon atoms such as ethylidene and isopropylidene, a cycloalkylidene group such as cyclohexylidene, or a tetrahydropyranylidene group. It is convenient that the protecting groups E$^1$ and E as taken together form an isopropylidene or a cyclohexylidene group.

In the aforesaid process of preparing the 5-deoxy-5-fluorokanamycin B derivative represented by the general formula (VII), the dialkylaminosulfur trifluoride of formula (VIII) is used as the fluorination agent, and it include typically diamethylaminosulfur trifluoride, diethylaminosulfur trifluoride (DAST) and dipropylaminosulfur trifluoride. Exemplary of the bis(-dialkylamino)-sulfur difluorides of formula (VIII') which may also be used as the fluorination agent are bis(dimethylamino)-sulfur difluoride and bis(diethylamino)-sulfur difluoride. All of these compounds are known fluorinating agents {see, for example, "J.Org.Chem.", 40, No. 5, 574-578 (1975)}.

The reaction between a compound of formula (VII) and a fluorination agent of formula (VIII) or (VIII') may be carried out in a non-polar organic solvent, for example, an aromatic hydrocarbon such as benzene, toluene and xylene or a halogenated hydrocarbon, preferably chlorinated hydrocarbon such as chloromethane, dichloromethane and chloroform, at a temperature in the range of −70° C.—+50° C., preferably at room temperature under an anhydrous condition. In general, the fluorination agent of formula (VIII) or (VIII') may be used in an amount of 1–10 moles per mole of the compound of formula (VII). An amine such as tertiary alkyl amine or pyridine may be present as the acid binding agent in the reaction mixture.

The step for the simultaneous fluorination and inversion of the 5-hydroxyl group in the process described above may alternatively be effected by sulfonylating the 5-hydroxyl group (for example, by alkylsulfonylating such as mesylating or trifluoromethylsulfonylating or by aralkylsulfonylating such as benzylsulfonylating), followed by subjecting the resulting 5-sulfonyloxy derivative to an action of a conventional fluorinating reagent, for example, a tetraalkylammonium fluoride (such as tetrabutylammonium fluoride), potassium fluoride and cesium fluoride, to remove the 5-sulfonyloxy group and introduce a fluoro-substituent simultaneously. Arylsulfonylation such as tosylation is not effective to achieve the intended sulfonylation of the 5-hydroxyl group. The sulfonylation reaction may be carried out by dissolving the starting compound of formula (VII) in a solvent such as pyridine, adding to the solution an alkylsulfonyl or aralkylsulfonyl halogenide such as methylsulfonyl chloride or benzylsulfonyl chloride or a corresponding anhydride in an amount of 1–10 molar equivalent and conducting the reaction at a temperature in the range of −20° C.−+100° C., preferably at room temperature under any anhydrous condition. The fluorination of the 5-O-sulfonyl derivative may also be effected in such solvent as ethylether, tetrahydrofuran, acetonitrile, dimethylformamide, sulfolane, hexamethyl phosphortriamide with the addition of an excess amount of a fluorinating agent such as tetraethyl- or tetrabutylammonium fluoride, cesium fluoride, or potassium fluoride containing a crown ether, at a temperature in the range of 0°–150° C.

After the completion of the fluorination of the 5-hydroxyl group, the reaction solution is added to an aqueous solution of an alkali metal carbonate or an alkali metal hydrogen carbonate, preferably an aqueous sodium hydrogen carbonate, to neutralize the acidic matters. The resulting mixture so neutralized is extracted with chloroform and the extract is washed with water, dried and concentrated under a reduced pressure to remove the chloroform and to leave the N,O-protected 5-deoxy-5-fluoro-kanamycin B derivative of the aforesaid formula (IX) as a solid.

The amino-protecting groups (B') and the hydroxyl-protecting groups (E, E$^1$ and G) in the compound of formula (IX) may be removed by a known deprotecting method, separately. Thus, an amino-protecting group of the alkoxycarbonyl or aryloxycarbonyl type may be removed by an alkaline hydrolysis, whereas an amino-protecting group of the aralkyloxycarbonyl type may be removed by an alkaline hydrolysis or by reduction. An amino-protecting group of the sulfonyl type may also be removed in a known manner by treating the compound of formula (IX) with metallic sodium in liquefied ammonia (see, for example, U.K. Pat. No. 1555661 and Japanese Patent Publication No. 29720/85). A hydroxyl-protecting group of the acyl type (E, E$^1$, G) may be removed by hydrolysis in an aqueous alkali metal hydroxide solution, e.g. an aqueous sodium hydroxide solution. In cases where E$^1$ and E as taken together form a single di-valent hydroxyl-protecting group of the alkylidene, cycloalkylidene or tetrahydropyranylidene type, such group may be removed by hydrolysis in the presence of an inorganic acid, an organic acid or a cation exchange resin of strongly acidic nature, e.g. a cation exchange resin of sulfonic acid type (see, for example, U.K. Pat. No. 2,043,634).

The removal of all the protective groups in the compound of formula (IX) results in the formation of the 5-deoxy-5-fluorokanamycin B derivatives of formula (VI). The isolation and purification of the compound of formula (VI) may suitably be effected by chromatography on a molecular sieve agent such as CM-Sephadex® C-25 (a product of Pharmacia Co.) as eluted with aqueous ammonia in a gradient elution technique.

The synthesis of 5-deoxy-5-fluorokanamycin A (the aforesaid Compound h) as illustrated in the Referential Example 2 given hereinbefore was also conducted in a similar way to the above-explained process of preparing the 5-deoxy-5-fluorokanamycin B derivatives represented by the general formula (VI) shown above. Referential Example 3–8 given hereinafter illustrates the preparation of a starting compound of the general formula (II) to be used in the process according to the third aspect of this invention.

REFERENTIAL EXAMPLE 3

(A) Preparation of 3',4',2",4",6"-penta-O-acetyl-1,3,2',6',3"-penta-N-tosylkanamycin B [Compound (31)]

1,3,2',6',3"-Penta-N-tosylkanamycin B (110 mg) was dissolved in dry pyridine (2.2 ml) to which acetyl chloride (0.062 ml) was added at 0° C., followed by effecting the reaction at 0° C. Two hours later, acetyl chloride (0.029 ml) was added further, followed by effecting further reaction for 3 hours (for the acetylation). Water (0.12 ml) was thereafter added to the reaction solution as obtained. The resultant mixture was concentrated and the residue was extracted with chloroform. The extract was washed with a saturated aqueous solution of sodium hydrogen carbonate, washed with water, and then dried over anhydrous sodium sulfate. The resulting solution was concentrated to dryness under reduced pressure, thereby affording the titled Compound (31) (147 mg).

Specific rotation $[\alpha]_D^{23}$: +25° (c 1.0, chloroform).

(B) Preparation of 3',4',2",4",6"-penta-O-acetyl-5-O-benzoyl-1,3,2',6',3"-penta-N-tosyl-5-epi-kanamycin B [Compound (32)]

Compound (31) (4.23 g) as obtained in the step (A) above was dissolved in dry tetrahydrofuran (64 ml), followed by successive addition of triphenylphosphine (2.27 g), diethyl azodicarboxylate (1.34 ml) and benzoic acid (1.06 g). The reaction was then conducted at room temperature. Two hours later, triphenylphosphine (2.27 g), diethyl azodicarboxylate (1.34 ml) and benzoic acid (1.06 g) were successively added again, and the reaction was further conducted overnight at room temperature (for effecting the Mitsunobu's reaction). The reaction mixture was concentrated to dryness and the residue was taken up in chloroform. The chloroform solution was washed successively with a saturated aqueous solution of sodium hydrogen carbonate and water and then dried over anhydrous sodium sulfate. The resultant solution was concentrated under reduced pressure. The residue was purified by column chromatography on silica gel (325 g; the column was developed with chloroform, followed by gradient elution with a mixed eluent of chloroform and ethanol while changing their ratio from 20:0 to 20:1), thereby affording the titled Compound (32) (2.38 g).

Specific rotation $[\alpha]_D^{23}$: +20° (c 1.0, chloroform).

$^1$H-NMR spectrum (in deuterochloroform in the presence of a drop of D$_2$O):
δ1.48 (1H, q, H-2ax),
δ1.54 (3H, s, Ac),
δ1.64 (3H, s, Ac),
δ1.84 (3H, s, Ac),
δ1.94 (3H, s, Ac),
δ1.97 (3H, s, Ac),
δ2.17 (1H, dt, H-2eq),
δ2.34 (3H, s, CH$_3$ of Ts),
δ2.38 (3H, s, CH$_3$ of Ts),
δ2.40 (3H, s, CH$_3$ of Ts),
δ2.47 (3H, s, CH$_3$ of Ts),
δ2.51 (3H, s, CH$_3$ of Ts),
δ3.78 (1H, dd, H-6),
δ6.01 (1H, bt, H-5).

(C) Preparation of 5-epi-1,3,2',6',3"-penta-N-tosylkanamycin B [Compound (33)]

Compound (32) (1.20 g) as obtained in the step (B) above was dissolved in a methanolic solution (24 ml) of sodium methoxide (0.2 mol/l), followed by effecting the reaction at 58° C. for 37 hours (for the removal of the acetyl and benzoyl groups). After adding dilute hydrochloric acid to the reaction mixture and neutralizing same, the resultant mixture was concentrated to dryness. The residue was washed with a large volume of water and then dried to afford the titled Compound (33) (0.930 g).

(D) Preparation of 3',4',2",4",6"-penta-O-acetyl-1,3,2',6',3"-penta-N-tosyl-5-epi-kanamycin B [Compound (34)]

wherein Ac means an acetyl group and Ts denotes a tosyl group, and Ac and Ts will hereinafter have the same meanings as above.

Compound (33) (898 mg) as obtained in the step (C) above was dissolved in dry pyridine (18 ml), followed by addition of acetyl chloride (0.77 ml) at 0° C. The reaction was made at 0° C. for 1 hour (for the protection of the hydroxyl groups by acetylation). The reaction mixture was added with water (0.97 ml) and concentrated to dryness. The residue was taken up in chloroform. The resulting solution was washed successively with a 10% aqueous solution of potassium hydrogen sulfate, a saturated aqueous solution of sodium hydrogen carbonate and water, and was then dried over anhydrous sodium sulfate. The solution was concentrated to dryness, thereby affording the titled Compound (34) as a colorless solid (1086 mg).

Specific rotation $[\alpha]_D^{23}$: +23° (c 1.0, chloroform).

$^1$H-NMR spectrum (in deuterochloroform):
δ1.60 (3H, s, Ac),
δ1.71 (3H, s, Ac),
δ1.93 (3H, s, Ac),
δ1.97 (3H, s, Ac),
δ2.02 (3H, s, Ac),
δ2.38 (6H, s, CH$_3$×2 of Ts),
δ2.40 (3H, s, CH$_3$ of Ts),
δ2.48 (3H, s, CH$_3$ of Ts),
δ2.49 (3H, s, CH$_3$ of Ts),

REFERENTIAL EXAMPLE 4

(A) Preparation of 3',4',2",4",6"-penta-O-acetyl-1,3,2',6',3"-penta-N-tosyl-5-deoxy-5-fluorokanamycin B [Compound (35)]

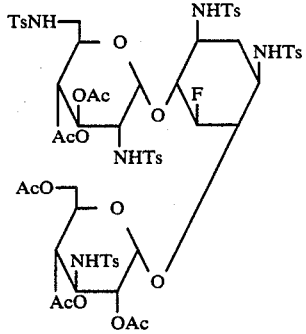

Compound (35)

Diethylaminosulfur trifluoride (DAST) (0.452 ml) was diluted with dry dichloromethane (17.4 ml) and dry pyridine (0.9 ml), to which was added at 0° C. a solution in dry dichloromethane (26 ml) of Compound (34) (1085 mg), which had been obtained in the step (D) of Referential Example 3. The reaction was effected at room temperature for 1.5 hours (for the fluorination and inversion of the epi-5-OH group). The reaction mixture was poured into an ice-cooled saturated aqueous solution of sodium hydrogen carbonate (45 ml). After throughly stirring the resultant mixture, the dichloromethane layer was taken out, washed successively with a saturated aqueous solution of sodium hydrogen carbonate and water, and dried over anhydrous sodium sulfate. The resultant dried solution was concentrated to dryness, thereby affording the titled Compound (35) as a solid (1.10 g).

$^{19}$F-NMR spectrum (in deuterochloroform in the presence of a drop of $D_2O$; internal standard: trichlorofluoromethane): −188.87 ppm (dt).

(B) Preparation of 5-deoxy-5-fluorokanamycin B

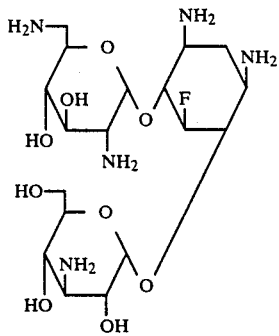

Compound (35) (1.1 g) as obtained in the step (A) above was dissolved in liquefied ammonia (300 ml) at −60° C., to which metal sodium (about 1.1 g) was then added. The reaction was conducted at −50° C. for 5 minutes (for the removal of the tosyl groups). Methanol (30 ml) was added to the reaction mixture, followed by evaporation of the ammonia. After concentration of the reaction mixture under reduced pressure, the residue was dissolved in water (110 ml) and then heated at 50° C. for 30 minutes (for the removal of the acetyl groups). The resulting reaction mixture was cooled to room temperature, to which "Dowex 50W×2 Resin" (trade name; 80 ml) was added to adsorb the resultant deprotected reaction product thereon. The deprotected reaction product which was adsorbed by the resin was placed together with resin on the top of a column of 40 ml of the same resin. After washing the column with water, the column was eluted with 1N aqueous ammonia, and the ninhydrin-positive fractions of the eluate were collected. In a column of "CM-Sephadex C-25" (trade name; 85 ml), the reaction product thus obtained was further developed gradiently with aqueous ammonia while changing the concentration of ammonia from 0N to 0.15N. Fractions of the eluate containing the intended compound were collected and concentrated. The titled Compound was obtained as a colorless solid (98 mg).

Specific rotation $[\alpha]_D^{23}$: +117° (c 0.6, water).

$^1$H-NMR spectrum (in deutero-hydrochloric acid; internal standard: sodium 3-(trimethylsilyl)-propionate-d$_4$):

δ2.08 (1H, q, H-2ax),
δ2.60 (1H, bdt, H-2eq),
δ3.31 (1H, dd, H-6'-a),
δ4.24 (1H, q, H-6 or H-4),
δ4.49 (1H, q, H-4 or H-6),
δ4.99 (1H, dt, H-5),
δ5.16 (1H, d, H-1"),
δ5.78 (1H, d, H-1').

REFERENTIAL EXAMPLE 5

(A) Preparation of 1,3,2',6',3"-penta-N-tosyltobramycin [Compound (36)]

Tobramycin, namely, 3'-deoxykanamycin B (600 mg) was dissolved in water (40 ml), into which sodium carbonate (900 mg) was added and dissolved. Dioxane (40 ml) was added further, followed by still further addition of tosyl chloride (1469 mg) under ice-cooling and stirring. 1.5 Hours later, sodium carbonate (450 mg) and tosyl chloride (735 mg) were again added to the reaction mixture obtained. Three hours later, sodium carbonate (450 mg) and tosyl chloride (735 mg) were added further. The reaction was effected overnight at room temperature (for the N-tosylation). The reaction mixture was concentrated to dryness, and the residue was washed with a large volume of water and then dried. The residue was thereafter dissolved in chloroform-ethanol, followed by reprecipitation with ethyl ether. A precipitate as deposited was washed with ethyl ether to afford the titled Compound (36) (1721 mg).

Specific rotation $[\alpha]_D^{23}$: +24° (c 1.0, pyridine).

(B) Preparation of 4",6"-O-cyclohexylidene-1,3,2',6',3"-penta-N-tosyltobramycin [Compound (37)]

Compound (36) (1.72 g) as obtained in the step (A) above was dissolved in dry dimethylformamide (35 ml), followed by addition of p-toluenesulfonic acid (60 mg) and 1,1-dimethoxycyclohexane (1.25 ml). Under reduced pressure of 30 mmHg, the reaction was conducted at 50° C. under stirring to achieve the 4",6"-O-cyclohexylidenation. The reaction mixture was cooled and poured into a saturated aqueous solution of sodium hydrogen carbonate (25 ml). The resulting mixture was concentrated to dryness. The residue was washed with a large volume of water and then dried. The residue was washed with ethyl ether to afford the titled Compound (37) (1.76 g).

Specific rotation $[\alpha]_D^{23}$: +3° (c 1, pyridine).

(C) Preparation of 4',2"-di-O-acetyl-4",6"-O-cyclohexylidene-1,3,2',6',3"-penta-N-tosyltobramycin

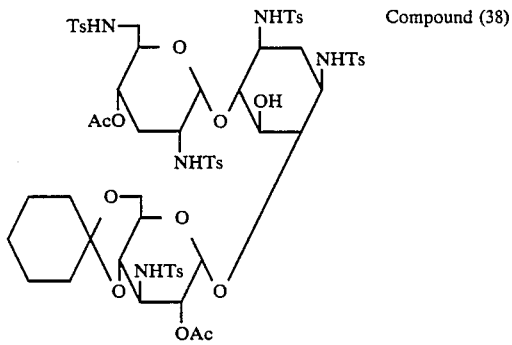

Compound (37) (1059 mg) as obtained in the step (B) above was dissolved in dry dimethylsulfoxide (4.8 ml), followed by addition of dry pyridine (0.53 ml) and N-acetylimidazole (356 mg). The reaction was made at 37° C. Upon elapsed time of 12 hours, 24 hours, 36 hours, 48 hours, 60 hours and 72 hours, 360 mg portions of N-acetylimidazole were added (for the protection of the hydroxyl groups by acetylation). 84 Hours later, water (2 ml) was added to the reaction mixture, and the resultant mixture was poured into a saturated aqueous solution of sodium hydrogen carbonate (106 ml). A precipitate as deposited was collected by filtration, washed with water, dried and then washed with ethyl ether, thereby to afford the titled Compound (38) (1084 mg).

Specific rotation $[\alpha]_D^{23}$: +18° (c 1.0, chloroform).

(D) Preparation of 4',2"-di-O-acetyl-5-O-benzoyl-4",6"-O-cyclohexylidene-1,3,2',6',3"-penta-N-tosyl-5-epi-tobramycin [Compound (39)]

Compound (38) (448 mg) as obtained in the step (C) above was dissolved in dry tetrahydrofuran (6.8 ml), followed by successive addition of triphenylphosphine (253 mg), diethyl azodicarboxylate (0.15 ml) and benzoic acid (119 mg). The reaction was made at room temperature. Two hours later, triphenylphosphine (253 mg), diethyl azobicarboxylate (0.15 ml) and benzoic acid (119 mg) were successively added again. The reaction was then effected overnight at room temperature (for the Mitsunobu's reaction. The resulting reaction solution was concentrated to dryness and the residue was dissolved in chloroform. The solution was washed successively with a saturated aqueous solution of sodium hydrogen carbonate and water and was then dried over anhydrous sodium sulfate. The solution was concentrated under reduced pressure. The residue was purified by chromatography on silica gel ["Merck Silica Gel 60" (trade name), 230-400 mesh, 30 g]; in such a way that the column was developed with chloroform, followed by gradient elution with a mixed eluent of chloroform and ethanol while changing their ratio from 20:0 to 20:1, thereby affording the titled Compound (39) (316 mg).

Specific rotation $[\alpha]_D^{23}$: −8° (c 1.0, chloroform).

$^1$H-NMR spectrum (in deuteropyridine-D$_2$O (20:1) at 80° C.):

δ1.78 (3H, s),
δ2.20 (6H, s),
δ2.28 (3H, s),
δ2.33 (3H, s),
δ2.36 (3H, s),

Each of the above peaks corresponds to CH$_3$ of Ac or Ts.

δ6.24 (1H, bt, H-5).

(E) Preparation of 4",6"-O-cyclohexylidene-1,3,2',6',3"-penta-N-tosyl-5-epi-tobramycin [Compound (40)]

Compound (39) (473 mg) as obtained in the step (D) above was dissolved in a methanolic solution (9.45 ml) of sodium methoxide (0.2 mol/l) to effect the reaction of 58° C. for 27 hours (for the removal of acetyl and benzoyl groups). Dilute hydrochloric acid was added to the reaction mixture to neutralize same. The resultant mixture was concentrated to dryness, and the residue was washed with a large volume of water and obtain the titled Compound (40) (418 mg).

(F) Preparation of 4',2"-di-O-acetyl-4",6"-O-cyclohexylidene-1,3,2',6',3"-penta-N-tosyl-5-epi-tobramycin [Compound (41)]

Compound (40) (3.97 g) as obtained in the step (E) above was dissolved in a mixture of dry dimethylsulfoxide (17.9 ml) and dry pyridine (2.0 ml), followed by addition of N-acetylimidazole (1.376 g). The reaction was effected at 37° C. Six hours later, N-acetylimidazole (1.391 g) was added, followed by reaction overnight at 37° C. (for the acetylation). After adding water (2.26 ml) to the reaction mixture, the resulting mixture was poured into a saturated aqueous solution of sodium hydrogen carbonate (400 ml). A precipitate deposited was collected by filtration, washed with water and washed with dry ethyl ether, thereby to afford the titled Compound (41) as a colorless solid (3.853 g). This compound is a novel compound.

Specific rotation $[\alpha]_D^{22}$: +19° (c 1.0, chloroform).

$^1$H-NMR spectrum (in deuteropyridine):

δ5.05 (1H, bs, H-5),
δ5.46 (1H, dd, H-2").

REFERENTIAL EXAMPLE 6

(A) Preparation of 4',2"-di-O-acetyl-4",6"-O-cyclohexylidene-1,3,2',6',3"-penta-N-tosyl-5-deoxy-5-fluorotobramycin [Compound (42)]

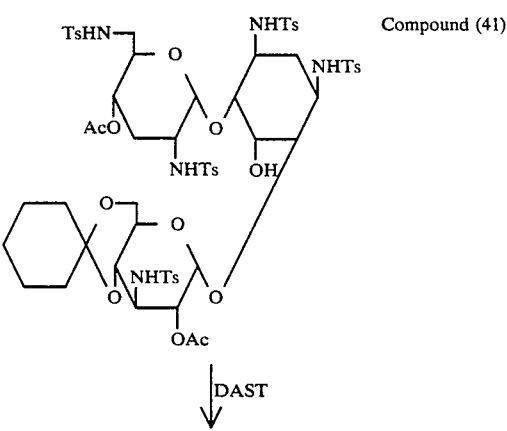

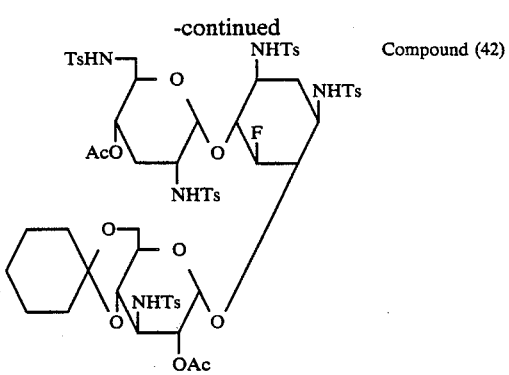

Compound (42)

Diethylaminosulfur trifluoride (DAST) (0.144 ml) was mixed with dry benzene (5.0 ml) and dry pyridine (0.29 ml), into which was then added at 0° C. a solution of Compound (41) (331 mg) in dry benzene (8.23 ml). The reaction was made at room temperature for 2 hours (for the fluorination and inversion of the epi-5-OH group). The reaction mixture obtained was poured into an ice-cooled saturated aqueous solution of sodium hydrogen carbonate (14 ml), followed by extraction with chloroform (30 ml). The resultant chloroform solution was washed successively with a saturated aqueous solution of sodium hydrogen carbonate and water, and was then dried over anhydrous sodium sulfate. The solution was concentrated to dryness under reduced pressure, thereby to afford the titled Compound (42) as a solid (363 mg).

Specific rotation $[\alpha]_D^{22}$: +21° (c 1.0, chloroform).

$^{19}$F-NMR spectrum (in deutero-pyridine-D$_2$O (20:1); internat standard: trichlorofluoroethane): −187.40 ppm.

(B) Preparation of 5-deoxy-5-fluorotobramycin, namely, 5,3'-dideoxy-5-fluorokanamycin B

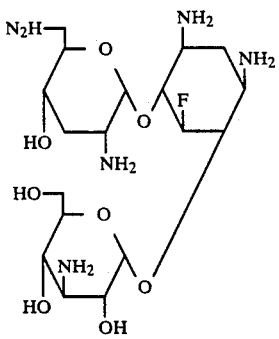

Compound (42) (393 mg) as obtained in the step (A) above was dissolved in liquefied ammonia (80 ml) at −60° C., to which metal sodium (about 400 mg) was added. The reaction was made at −50° C. for 5 minutes (for the removal of tosyl groups). Methanol (10 ml) was added to the reaction mixture, followed by evaporation of ammonia. After concentration of the reaction mixture under reduced pressure, the residue was dissolved in water (40 ml) and then heated at 50° C. for 30 minutes (for the removal of acetyl groups). The resulting reaction mixture was cooled to room temperature, to which "Dowex 50W×2" resin (trade name; 60 ml) was added to adsorb the reaction product thereon (the removal of the cyclohexylidene group took place then). The resultant deprotected reaction product as adsorbed by the resin was placed on the top of a column of 20 ml of the same resin. After washing the column with water, the column was eluted with 1N aqueous ammonia, and the ninhydrin-positive fractions of the eluate were collected. In a column of "CM-Sephadex C-25" (trade name; 26 ml), the reaction product obtained was further developed gradiently with aqueous ammonia while changing the concentration of ammonia from 0N to 0.15N. Fractions containing the intended compound were collected and concentrated. The titled Compound was obtained as a colorless solid (55.6 mg).

Specific rotation $[\alpha]_D^{23}$: +124° (c 1.0, water).

$^1$H-NMR spectrum (in 20% aqueous deutero-ammonia; internal standard: sodium 3-(trimethylsilyl)-propionate-d$_4$):

δ1.28 (1H, q, H-2ax),
δ1.60 (6H, q, H-3'ax),
δ3.30 (1H, t, H-4″),
δ4.57 (1H, dt, H-5),
δ5.01 (1H, d, H-1″),
δ5.09 (1H, d, H-1').

REFERENTIAL EXAMPLE 7

(A) Preparation of 1,3,2',6',3''-penta-N-tosyl-3',4'-dideoxykanamycin B {Compound (43)} In water (35 ml) was dissolved 3',4'-dideoxykanamycin B (namely dibekacin) sulfate (3.50 g; potency: 690 μg/mg), followed by addition of sodium carbonate (3.40 g; 6 mole equivalents). Thereafter, 1,4-dioxane (70 ml) was added, and p-toluenesulfonyl chloride (6.12 g; 6 mole equivalents based on the dibekacin) was added further under ice-cooling and stirring. One hour later, the reaction mixture was heated to room temperature, followed by further stirring. 72 Hours later, the reaction mixture was concentrated under reduced pressure, followed by addition of water (300 ml). The resulting precipitate was collected by filtration, washed with water and then dried under reduced pressure. The precipitate was washed further with ethyl ether and dried under reduced pressure, thereby affording the titled Compound (43) as a solid (6.06 g). Yield: 93%.

(B) Preparation of 4'',6''-O-cyclohexylidene-1,3,2',6',3''-penta-N-tosylidibekacin [Compound (44)]

Compound (43) (1.63 g) as obtained in the step (A) above was dissolved in dry DMF (8.1 ml), to which were added cyclohexanone dimethylacetal (1 ml) and p-toluenesulfonic acid (51 mg). The mixture obtained was stirred at 50° C. under reduced pressure of 30 mmHg. One hour later, the resulting reaction solution was poured into an ice-cooled saturated aqueous solution of sodium hydrogen carbonate (200 ml). A white precipitate thus formed was collected by filtration, washed with water and then dried under reduced pressure, thereby affording the titled Compound (44) as a white solid (1.75 g). The yield was stoichiometric.

Specific rotation $[\alpha]_D^{24}$: +28° (c 1.0, DMF).

(C) Preparation of 2''-O-benzoyl-4'',6''-O-cyclohexylidene-1,3,2',6',3''-penta-N-tosyldibekacin [Compound (45)]

Compound (44) (1.75 g) as obtained in the step (B) above was dissolved in dry pyridine (35 ml), to which benzoyl chloride (0.78 ml) was added at 0° C. under stirring so as to conduct a reaction. Water (0.6 ml) was added 3.5 hours later. After allowing the reaction mixture to stand for 1 hour, it was concentrated under reduced pressure. The residue was extracted with chloroform. The resulting chloroform solution was washed successively with a saturated aqueous solution of sodium hydrogen carbonate (100 ml×3), a 5% aqueous solution of potassium hydrogen sulfate (100 ml×2) and water (100 ml×3), dried over anhydrous sodium sulfate and then concentrated to dryness to obtain the titled Compound (45) as a solid (1.885 g). Yield: 99.5%.

Specific rotation $[\alpha]_D^{22}$: +32° (c 1, CHCl$_3$).

(D) Preparation of 5,2''-di-O-benzoyl-4'',6''-O-cyclohexylidene-1,3,2',6',3'''-penta-N-tosyl5-epi-dibekacin [Compound (46)]Compound (45) (1.62 g) as obtained in the step (C) above was dissolved in dry tetrahydrofuran (24.3 ml), followed by addition of diethyl azodicarboxylate (DEAD) (0.54 ml), triphenylphosphine [P(C$_6$H$_5$)$_3$] (906 mg) and benzoic acid (422 mg). The reaction was made at 50° C. 1.5 Hour later, the same reagents were added respectively in the same amounts. The results reaction mixture was cooled down to room temperature and was allowed to undergo the reaction. Three hours later, the same reagents were again added respectively in the same amounts as above. The reaction mixture was heated to 50° C., and 5 hours later, it was cooled to room temperature, at which the reaction was carried out overnight. 21 Hours later, the same reagents were added further respectively in the same amounts, followed by effecting the reaction at room temperature (for the Mitsunobu's reaction). 92 Hours later, the reaction mixture was concentrated under reduced pressure, the resulting syrup was dissolved in chloroform (300 ml), washed successively with a saturated aqueous solution of sodium hydrogen carbonate (200 ml×2) and water (200 ml×3), dried over anhydrous sodium sulfate, and then concentration to dryness. A solid obtained (9.68 g) was subjected to column chromatography on silica gel ("Wako-gel C-200", trade name; as developed with a mixed solvent of toluene and acetone) to repeat removal of the remaining reagents and separation and purification of the reaction product, thereby affording the titled Compound (46) as a yellow solid (0.95 g). Yield: 54.5%.

(E) Preparation of 4'',6''-O-cyclohexylidene-1,3,2',6',3'''-penta-N-tosyl-5-epi-dibekacin

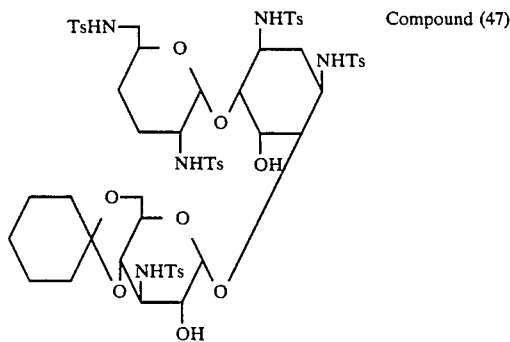

Compound (47)

Compound (46) (0.95 g) as obtained in the step (D) above was mixed with methanol (19 ml) (with a gellation occurring), to which a 28% methanolic solution of sodium methoxide (0.7 ml) was then added to conduct the reaction at 50° C., when a homogeneous solution was formed. After conducting this debenzoylation reaction for 44 hours, the reaction mixture was concentrated under reduced pressure, and a 0.25% aqueous solution of potassium hydrogen sulfate (20 ml) was added to the residue. A white precipitate obtained was collected by filtration, washed with water and dried under reduced pressure, thereby affording the titled Compound (47) as a white solid (0.83 g). The yield was stoichiometric.

Specific rotation $[\alpha]_D^{23}$: +6° [c 0.5, acetonemethanol (1:1)]

(F) Preparation of 2''-O-benzoyl-4'',6''-O-cyclohexylidene-1,3,2',6',3'''-penta-N-tosyl-5-epi-dibekacin [Compound (48)]

Compound (47) (0.77 g) as obtained in the step (E) above was dissolved in dry pyridine (15.4 ml). At 0° C. and under stirring, benzoyl chloride [0.34 ml, 5 mole equivalents based on Compound (47)] was added to the solution to conduct a reaction (for the 2''-O-benzoylation). Water (0.26 ml) was added 30 minutes later. One hour later, the reaction mixture was concentrated under reduced pressure. The residue was dissolved in chloroform (100 ml), washed successively with a saturated aqueous solution of sodium hydrogen carbonate (50 ml×2), a 5% aqueous solution of potassium hydrogen sulfate (50 ml×3) and water (50 ml×2), dried over anhydrous sodium sulfate and then concentrated to dryness, so that the titled Compound (48) was obtained as a solid (0.84 g). The yield was stoichiometric.

Specific rotation $[\alpha]_D^{23}$: +29° (c 1, CHCl$_3$).

REFERENTIAL EXAMPLE 8

(A) Preparation of 2''-O-benzoyl-4'',6''-O-cyclohexylidene-1,3,2',6',3'''-penta-N-tosyl-5-deoxy-5-fluorodibekacin [Compound (49)]

Dry pyridine (0.66 ml) was added to dry benzene (15.4 ml), followed by addition of diethylaminosulfur trifluoride (DAST) [0.33 ml, 5 mole equivalents based on Compound (48)] at 0° C. under stirring. To the resulting mixture was added Compound (48) (0.77 g) as obtained in the step (F) of Referential Example 4, and then the reaction was made at room temperature under nitrogen atmosphere. One hour later, the reaction mixture was ice-cooled and then poured into a saturated aqueous solution of sodium hydrogen carbonate (26 ml). The resultant mixture was extracted with chloroform (80 ml). The organic liquid layer obtained was washed successively with a saturated aqueous solution of sodium hydrogen carbonate (40 ml×1), a 5% aqueous solution of potassium hydrogen sulfate (25 ml×3), a saturated aqueous solution of sodium hydrogen carbonate (25 ml×2) and water (25 ml×3), dried over anhydrous sodium sulfate, and then concentrated to dryness, to afford the titled Compound (49) as a solid (0.79 g). The yield was stoichiometric.

Specific rotation $[\alpha]_D^{23}$: +37° (c 1, CHCl$_3$).

(B) Preparation of 5-deoxy-5-fluorodibekacin, namely, 5,3',4'-trideoxy-5-fluorokanamycin B

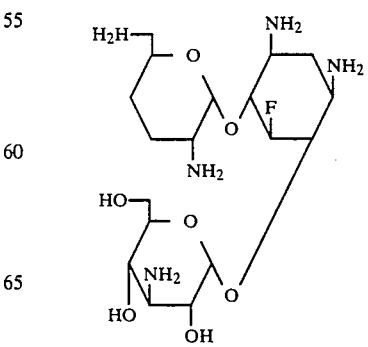

Compound (49) (0.74 g) as obtained in the step (A) above was dissolved in methanol (14.8 ml), to which a 28% methanolic solution of sodium methoxide (0.55 ml) was added, followed by effecting the reaction at room temperature (for the de-benzoylation). Two hours later, the reaction mixture was neutralized by mixing with a resin, "Dowex 50W×2" (trade name, H+-form, 4 ml) which had been saturated with methanol. The mixture was filtered to remove the resin, which was then washed with methanol. The filtrate and washing were combined together and then concentrated to dryness, thereby affording 0.59 g of a pale yellow solid (yield: 87%).

The solid reaction product so de-benzoylated (0.59 g) was added with 80% acetic acid (12 ml), followed by effecting the reaction at 80° C. (for the de-cyclohexylidenization). 30 Minutes later, the reaction mixture was cooled down to room temperature and concentrated to dryness, thereby obtaining 0.52 g of a pale yellow solid (yield: 93%).

The solid, de-cyclohexylidenized product (0.52 g) was dissolved in liquefied ammonia (about 100 ml) at −50° C. Metal sodium (about 500 mg) was added thereto with vigorous stirring to conduct the de-tosylation reaction. 5 Minutes later, methanol was added until the blue color of the mixture disappeared. The reaction mixture was heated to room temperature and ammonia was allowed to evaporate off. The residue was dried under reduced pressure to obtain a solid comprising the de-tosylated product. The solid was then dissolved in water (23 ml), followed by neutralization with "Dowex 50W×2" (trade name, H+-form, 25 ml). The resin containing the de-tosylated product adsorbed therein was charged on the top of a column of 10 ml of the same resin. After washing the column with water, the column was eluted with 1N aqueous ammonia and the ninhydrin-positive fractions of the eluate were combined together and concentrated to dryness. The resulting solid (0.18 g) was dissolved in water (180 ml) and the resulting solution was charged into a column of "CM-Sephadex C-25" (trade name, NH$_4$+form, 90 ml). After washing the Sephadex column with water, the column was eluted gradiently with aqueous ammonia while changing the concentration of ammonia from 0.05N to 0.2N. The active fractions of the eluate were combined and concentrated to dryness, to give 0.10 g of the titled Compound a white solid (yield: 46% as monocarbonatemonohydrate).

Specific rotation $[\alpha]_D^{24}$: +122° (c 1, water).

$^1$H-NMR (250 MHz, 20%ND$_3$-D$_2$O, standard: TMS):

$\delta$4.55 (dt, H-5, $J_{5,F}$=51.5 Hz, $J_{5,4}$=8.5 or 9.5 Hz, $J_{5,6}$=9.5 or 8.5 Hz)

$\delta$5.01 (d, H-1″, $J_{1″,2″}$=3.8 Hz), $\delta$5.09 (d, H-1″, $J_{1',2'}$=3.5 Hz).

We claim:

1. A 1-N-{(2R,3R)-4-amino-3-fluoro-2-hydroxybutyryl}kanamycin A or B derivative represented by the formula:

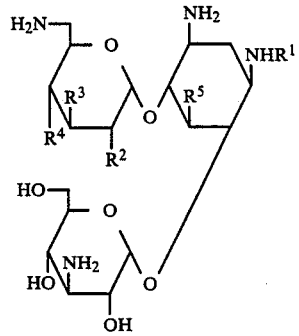

wherein $R^1$ means a (2R,3R)-4-amino-3-fluoro-2-hydroxybutyryl group of the formula:

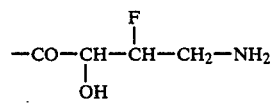

and (a) $R^2$, $R^3$, $R^4$ and $R^5$ are each a hydroxyl group, or (b) $R^4$ and $R^5$ are each a hydroxyl group, and $R^2$ and $R^3$ are each a hydrogen atom, or (c) $R^4$ and $R^5$ are each a hydroxyl group, $R^3$ is a hydrogen atom, and $R^2$ is a fluorine atom, or (d) $R^2$, $R^3$ and $R^4$ are each a hydroxyl group, and $R^5$ is a fluorine atom, or (e) $R^2$ is an amino group, and $R^3$, $R^4$ and $R^5$ are each a hydroxyl group, or (f) $R^2$ is an amino group, $R^3$ is a hydrogen atom, and $R^4$ and $R^5$ are each a hydroxyl group, or (g) $R^2$ is an amino group, $R^3$ and $R^4$ are each a hydrogen atom, and $R^5$ is a hydroxyl group, or (h) $R^2$ is an amino group, $R^3$ and $R^4$ are each a hydroxyl group, and $R^5$ is a fluorine atom, or (i) $R^2$ is an amino group, $R^3$ is a hydrogen atom, $R^4$ is a hydroxyl group, and $R^5$ is a fluorine atom, or (j) $R^2$ is an amino group, $R^3$ and $R^4$ are each a hydrogen atom, and $R^5$ is a fluorine atom; or a pharmaceutically acceptable acid addition salt thereof.

2. A compound of claim 1, which is 1-N-{(2R,3R)-4-amino-3-fluoro-2-hydroxybutyryl}-kanamycin A.

3. A compound of claim 1, which is 1-N-{(2R,3R)-4-amino-3-fluoro-2-hydroxybutyryl}-2′,3′-dideoxykanamycin A.

4. A compound of claim 1, which is 1-N-{(2R,3R)-4-amino-3-fluoro-2-hydroxybutyryl}-2′,3′-dideoxy-2′-fluorokanamycin A.

5. A compound of claim 1, which is 1-N-{(2R,3R)-4-amino-3-fluoro-2-hydroxybutyryl}-5-deoxy-5-fluorokanamycin A.

6. A compound of claim 1, which is 1-N-{(2R,3R)-4-amino-3-fluoro-2-hydroxybutyryl}-kanamycin B.

7. A compound of claim 1, which is 1-N-{(2R,3R)-4-amino-3-fluoro-2-hydroxybutyryl}-3′-deoxykanamycin B.

8. A compound of claim 1, which is 1-N-{(2R,3R)-4-amino-3-fluoro-2-hydroxybutyryl}-3′,4′-dideosykanamycin B.

9. A compound of claim 1, which is 1-N-{(2R,3R)-4-amino-3-fluoro-2-hydroxybutyryl}-5-deoxy-5-fluorokanamycin B.

10. A compound of claim 1, which is 1-N-{(2R,3R)-4-amino-3-fluoro-2-hydroxybutyryl}-5,3′-dideoxy-5-fluorokanamycin B.

11. A compound of claim 1, which is 1-N-{(2r,3R)-4-amino-3-fluoro-2-hydroxybutyryl}-5,3′,4′-trideoxy-5-fluorokanamycin B.

12. A pharmaceutical composition comprising a compound of the formula (I) as defined in claim 1 or a pharmaceutically acceptable acid addition salt thereof, as the active ingredient in an antibacterially effective amount, in association with a pharmaceutically acceptable solid or liquid carrier for the active ingredient.

13. A method of treating bacterial growth in an animal or human, which comprises administering a bacteriocidally effective amount of the compound of the formula (I) as defined in claim 1 or a pharmaceutically acceptable acid addition salt thereof to an animal or human infected with or susceptible to bacteria.

* * * * *